(12) United States Patent
Cowperthwait et al.

(10) Patent No.: US 12,336,714 B1
(45) Date of Patent: Jun. 24, 2025

(54) WIRELESS ARRAYS FOR SURGICAL STAPLERS

(71) Applicant: CILAG GMBH INTERNATIONAL, Zug (CH)

(72) Inventors: Matthew D. Cowperthwait, Cincinnati, OH (US); Logan R. Rose, Loveland, OH (US); Christopher Denzinger, Cincinnati, OH (US); Shane R. Adams, Lebanon, OH (US); Eric Lafay, Madeira, OH (US)

(73) Assignee: CILAG GMBH INTERNATIONAL, Zug (CH)

( * ) Notice: Subject to any disclaimer, the term of this patent is extended or adjusted under 35 U.S.C. 154(b) by 4 days.

(21) Appl. No.: 18/394,795

(22) Filed: Dec. 22, 2023

(51) Int. Cl.
*A61B 17/64* (2006.01)
*A61B 17/115* (2006.01)
*A61B 17/00* (2006.01)

(52) U.S. Cl.
CPC . *A61B 17/1155* (2013.01); *A61B 2017/00221* (2013.01); *A61B 2017/00367* (2013.01); *A61B 2017/00734* (2013.01); *A61B 2017/00982* (2013.01)

(58) Field of Classification Search
CPC ...... A61B 17/1155; A61B 2017/00221; A61B 2017/00367; A61B 2017/00734; A61B 2017/00982
See application file for complete search history.

(56) References Cited

U.S. PATENT DOCUMENTS

| | | | |
|---|---|---|---|
| 8,657,174 B2* | 2/2014 | Yates | A61B 90/98 320/132 |
| 9,358,003 B2 | 6/2016 | Hall | |
| 2011/0288573 A1* | 11/2011 | Yates | A61B 50/36 227/175.1 |
| 2013/0041371 A1* | 2/2013 | Yates | A61B 18/1445 606/45 |
| 2017/0290583 A1* | 10/2017 | Reed | A61B 17/2909 |
| 2018/0132849 A1 | 5/2018 | Miller | |
| 2018/0326144 A1* | 11/2018 | Truckai | A61B 18/1485 |
| 2019/0200998 A1* | 7/2019 | Shelton, IV | A61B 5/0066 |
| 2022/0233241 A1* | 7/2022 | Shelton, IV | A61B 5/7405 |
| 2022/0278438 A1 | 9/2022 | Shelton, IV | |
| 2023/0138743 A1* | 5/2023 | Ross | A61B 18/00 455/41.2 |

* cited by examiner

*Primary Examiner* — Eyamindae C Jallow
(74) *Attorney, Agent, or Firm* — TROUTMAN PEPPER LOCKE LLP

(57) ABSTRACT

The present disclosure provides a circular stapler. The circular stapler includes a stapling head assembly, an anvil detachably attachable to the stapling head assembly, and a handle assembly. The handle assembly includes a handle controller, a connector, and handle transceiver configured to wirelessly transmit a first signal to an external hub. The handle transceiver is separated from the handle controller and is in electrical communication with the handle controller via the connector.

20 Claims, 21 Drawing Sheets

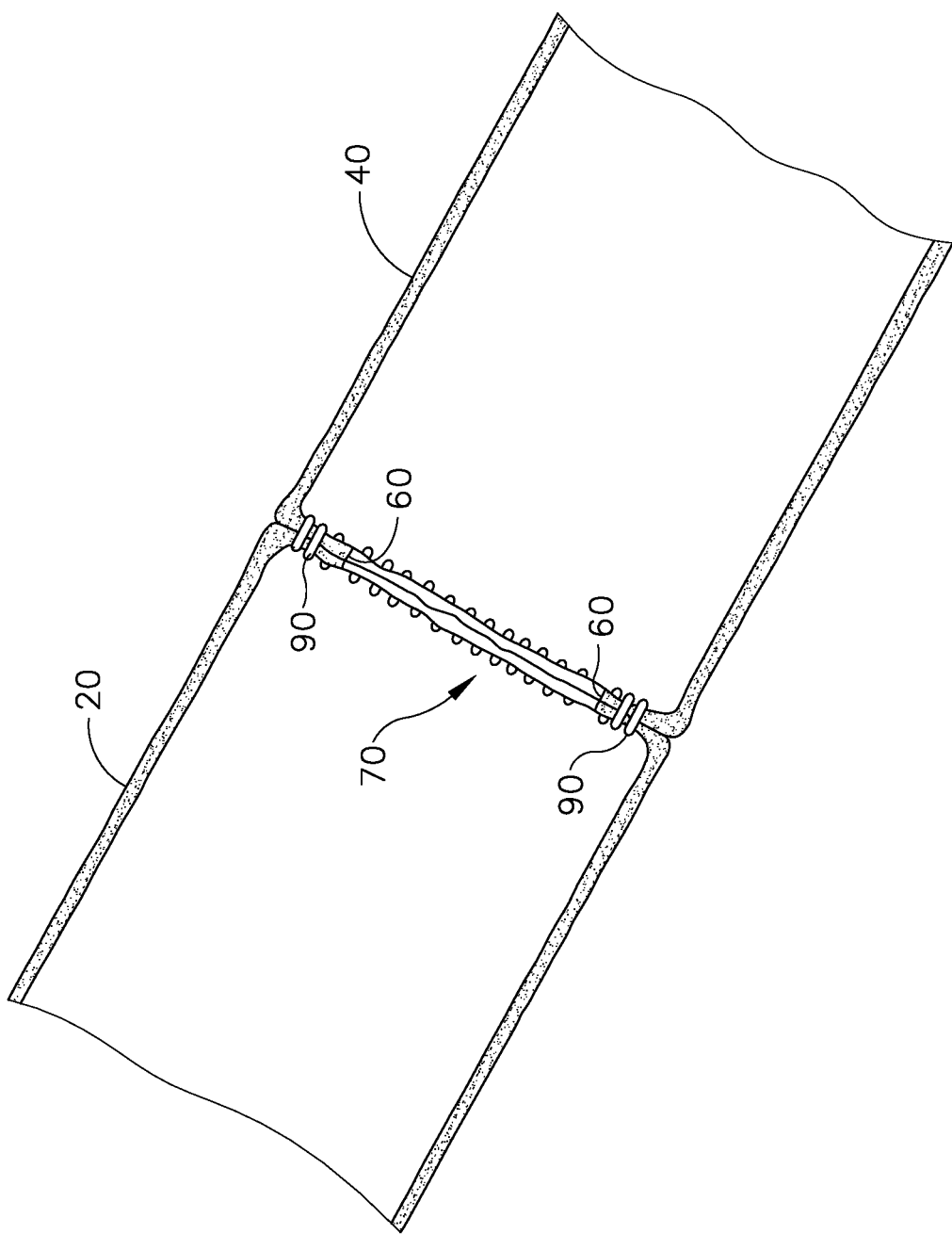

WIRELESS ARRAYS FOR SURGICAL STAPLERS

FIELD OF THE INVENTION

The present disclosure generally describes surgical instruments with a plurality of transceivers that can communicate information from the end of the surgical instrument and, more particularly, to surgical staplers with an anvil transceiver and a handle transceiver that receives signals from the anvil transceiver.

BACKGROUND

In some surgical procedures (e.g., colorectal, bariatric, thoracic, etc.), portions of a patient's digestive tract (e.g., the gastrointestinal tract and/or esophagus, etc.) may be cut and removed to eliminate undesirable tissue or for other reasons. Once the tissue is removed, the remaining portions of the digestive tract may be coupled together in an end-to-end anastomosis. The end-to-end anastomosis may provide a substantially unobstructed flow path from one portion of the digestive tract to the other portion of the digestive tract, without also providing any kind of leaking at the site of the anastomosis.

One example of an instrument that may be used to provide an end-to-end anastomosis is a circular stapler. Some such staplers are operable to clamp down on layers of tissue, cut through the clamped layers of tissue, and drive staples through the clamped layers of tissue to substantially seal the layers of tissue together near the severed ends of the tissue layers, thereby joining the two severed ends of the anatomical lumen together. The circular stapler may be configured to sever the tissue and seal the tissue substantially simultaneously. For instance, the circular stapler may sever excess tissue that is interior to an annular array of staples at an anastomosis, to provide a substantially smooth transition between the anatomical lumen sections that are joined at the anastomosis. Circular staplers may be used in open procedures or in endoscopic procedures. In some instances, a portion of the circular stapler is inserted through a patient's naturally occurring orifice.

The distal end of the circular stapler is, therefore, positioned within the patient. The distal end can include a stapling head assembly that can generate different types of digital information. One issue inherent with circular staplers, therefore, is that the distal end is separable from the proximal, handle end and as such it is difficult to send this digital information from the stapling head assembly to an external device, such as a computer in the operating room. A need exists, therefore, for improved circular stapler designs that can improve signal transmission from the stapling head assembly inside the patient to an external hub.

BACKGROUND

The present disclosure provides solutions to the needs mentioned above. One aspect of the present disclosure provides a surgical apparatus. The apparatus can include a stapling head assembly. The apparatus can include an anvil detachably attachable to the stapling head assembly. The apparatus can include a handle assembly. The handle assembly can include a handle controller, a connector, and a handle transceiver configured to wirelessly transmit a first signal to an external hub. The handle transceiver can be separated from the handle controller and can be in electrical communication with the handle controller via the connector.

In any of the embodiments described herein, the handle assembly can include a knob rotatable to adjust a gap distance between anvil surface and the handle assembly. The handle transceiver can be positioned within the knob.

In any of the embodiments described herein, the handle assembly can include a pistol grip. The handle transceiver can be positioned within the pistol grip.

In any of the embodiments described herein, the handle transceiver can be encased within a shroud to shield the handle transceiver from signal noise from a motor.

In any of the embodiments described herein, the handle assembly can include a battery housing including a battery and a housing cavity sized to accept the battery housing. The battery housing can be insertable and removable from the housing cavity. The handle transceiver can be positioned on the battery housing.

In any of the embodiments described herein, the handle assembly can include a first connector positioned on the battery housing and in electrical communication with the handle transceiver and a second connector positioned within the housing cavity and in electrical communication with the handle controller. The first connector and the second can be configured to contact one another when the battery housing can be positioned within the housing cavity.

In any of the embodiments described herein, the handle assembly can include a battery housing including a battery and a housing cavity sized to accept the battery housing. The battery housing can be insertable and removable from the housing cavity. The handle transceiver can be positioned within the housing cavity.

In any of the embodiments described herein, the handle assembly can include a display positioned on a display panel visible from an exterior of the handle assembly. The handle transceiver can be positioned on the display panel.

In any of the embodiments described herein, the anvil can be removably attached to the stapling head assembly and can include one or more sensors configured to output signals to the handle controller.

In any of the embodiments described herein, the anvil can include an anvil transceiver. The one or more sensors can be configured to generate a second signal comprising first sensor data. The one or more sensors can be configured to transmit the first signal to the anvil transceiver. The handle transceiver can be configured to communicate wirelessly with the anvil transceiver and can be operable as a wireless relay between the anvil transceiver and the external hub.

One aspect of the present disclosure provides a surgical apparatus. The apparatus can include a stapling head assembly. The stapling head assembly can include a deck surface, an array of staple openings formed through the deck surface, and a plurality of staples associated with the array of staple openings. The stapling head assembly can be operable to drive the staples through the array of staple openings. The apparatus can include an anvil detachably attachable to the stapling head assembly. The anvil can include an anvil surface configured to compress tissue against the deck surface. The anvil surface can define an array of staple forming pockets. The anvil can include an anvil power source. The anvil can include an anvil transceiver. The apparatus can include a handle assembly. The handle assembly can include a handle controller and a handle transceiver configured to communicate wirelessly with both the anvil transceiver and an external hub. The handle transceiver can be operable as a wireless relay to receive a first signal from the anvil transceiver and transmit a second signal to the external hub.

In any of the embodiments described herein, the anvil further can include a position sensor operable to detect an orientation of the anvil within a patient. The first signal can include information related to the orientation of the anvil.

In any of the embodiments described herein, the anvil further can include a surface sensor positioned on the anvil surface. The surface sensor can be operable to detect contact of tissue upon the anvil surface. The first signal can include information related to the contact.

In any of the embodiments described herein, the surface sensor can be one of a plurality of surface sensors. The plurality of surface sensors can be configured to detect compression of tissue between the anvil surface and the deck surface.

In any of the embodiments described herein, the anvil further can include a plurality of staple pocket sensors, each staple pocket sensor positioned within one of the staple forming pockets and configured to detect contact by a staple. The first signal can include information from one or more of the plurality of staple pocket sensors.

In any of the embodiments described herein, the handle assembly can include a knob rotatable to adjust a gap distance between anvil surface and the deck surface. The handle transceiver can be positioned within the knob.

In any of the embodiments described herein, the handle assembly can include a pistol grip. The handle transceiver can be positioned within the pistol grip.

In any of the embodiments described herein, the handle transceiver can be encased within a shroud to shield the handle transceiver from signal noise from a motor.

In any of the embodiments described herein, the handle assembly can include a battery housing including a battery. The handle assembly can include a housing cavity sized to accept the battery housing. The battery housing can be insertable and removable from the housing cavity. The handle transceiver can be positioned on the battery housing.

In any of the embodiments described herein, the handle assembly can include: a first connector positioned on the battery housing an in electrical communication with the handle transceiver, and can include a second connector positioned within the housing cavity and in electrical communication with the handle controller. The first connector and the second connector can be configured to contact one another when the battery housing can be positioned within the housing cavity.

In any of the embodiments described herein, the handle assembly can include a battery housing including a battery, and a housing cavity sized to accept the battery housing. The battery housing can be insertable and removable from the housing cavity. The handle transceiver can be positioned within the housing cavity.

In any of the embodiments described herein, the handle assembly can include a display positioned on a display panel visible from an exterior of the handle assembly. The handle transceiver can be positioned on the display panel.

In any of the embodiments described herein, the first signal and the second signal can be transmitted at different frequencies.

One aspect of the present disclosure provides a surgical apparatus. The apparatus can include a stapling head assembly. The apparatus can include an anvil detachably attachable to the stapling head assembly and comprising an anvil transceiver and one or more sensors. The one or more sensors can be configured to generate a first signal comprising first sensor data, and can be configured to transmit the first signal to the anvil transceiver for transmission by the anvil transceiver. The apparatus can include a handle assembly. The handle assembly can include a handle controller and a handle transceiver configured to communicate wirelessly with the anvil transceiver and receive the first signal.

In any of the embodiments described herein, the handle transceiver can be operable as a wireless relay to receive the first signal from the anvil transceiver and transmit a second signal to an external hub.

In any of the embodiments described herein, the second signal can include the first sensor data.

In any of the embodiments described herein, the first signal and the second signal can be transmitted at different frequencies.

In any of the embodiments described herein, the one or more sensors can include a position sensor operable to detect an orientation of the anvil within a patient. First sensor data can include information related to the orientation of the anvil.

In any of the embodiments described herein, the handle assembly can include: a battery housing including a battery and a housing cavity sized to accept the battery housing. The battery housing can be insertable and removable from the housing cavity. The handle transceiver can be positioned on the battery housing.

In any of the embodiments described herein, the handle assembly can include a display positioned on a display panel visible from an exterior of the handle assembly. The handle transceiver can be positioned on the display panel.

BRIEF DESCRIPTION OF THE DRAWINGS

While the specification concludes with claims which particularly point out and distinctly claim this technology, it is believed this technology will be better understood from the following description of certain examples taken in conjunction with the accompanying drawings, in which like reference numerals identify the same elements and in which:

FIG. 7E depicts a cross-sectional side view of the first and second sections of the digestive tract of FIG. 7A joined together at an end-to-end anastomosis, according to one aspect of the present disclosure;

Figure 1:
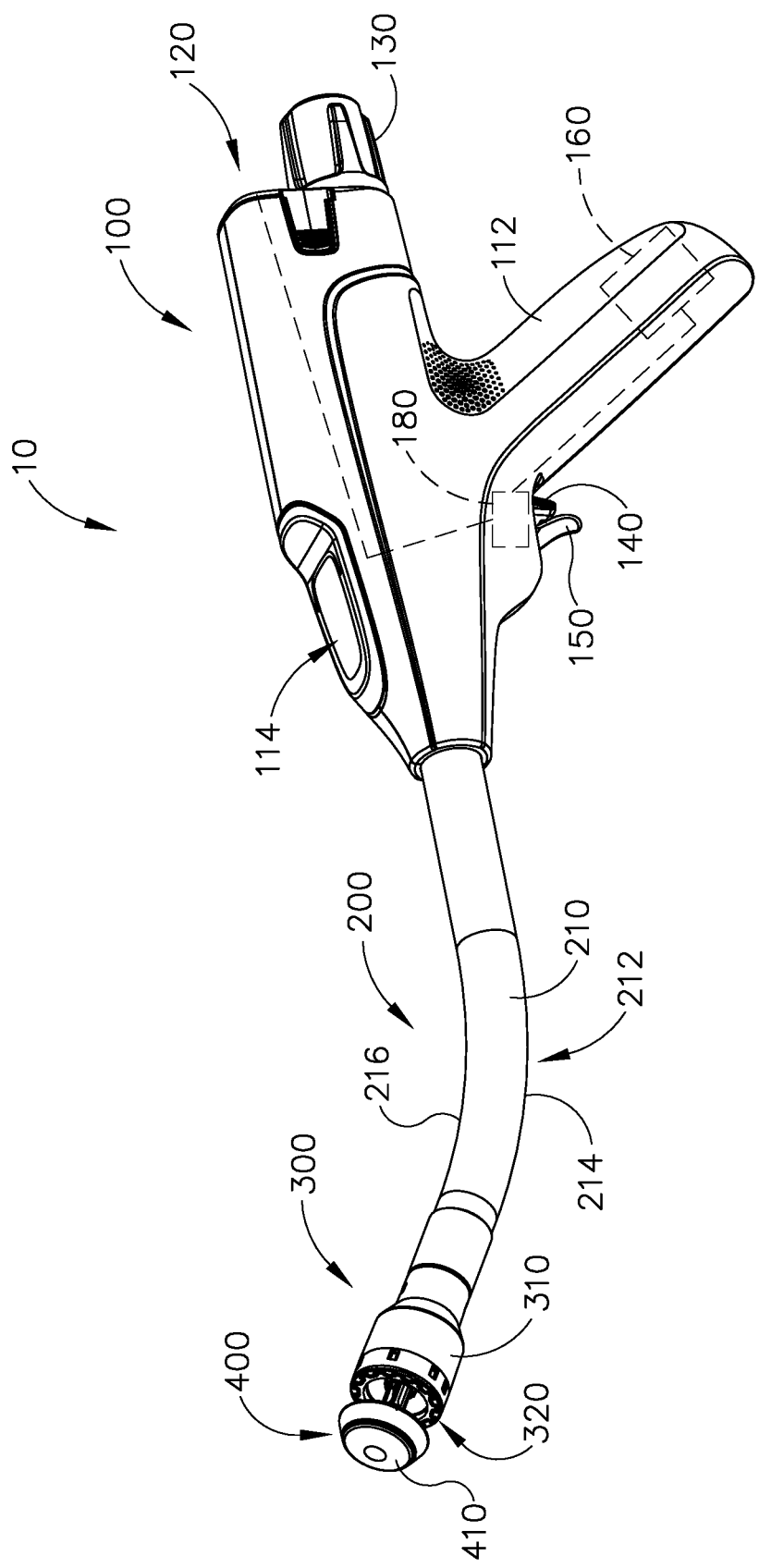
FIG. 1 depicts a perspective view of an exemplary circular stapler, according to one aspect of the present disclosure.

The drawings are not intended to be limiting in any way, and it is contemplated that various embodiments of the technology may be carried out in a variety of other ways, including those not necessarily depicted in the drawings. The accompanying drawings incorporated in and forming a part of the specification illustrate several aspects of the present technology, and together with the description serve to explain the principles of the technology; it being understood, however, that this technology is not limited to the precise arrangements shown.

DETAILED DESCRIPTION

The following description of certain examples of the technology should not be used to limit its scope. Other examples, features, aspects, embodiments, and advantages of the technology will become apparent to those skilled in the art from the following description, which is by way of illustration, one of the best modes contemplated for carrying out the technology. As will be realized, the technology described herein is capable of other different and obvious aspects, all without departing from the technology. Accordingly, the drawings and descriptions should be regarded as illustrative in nature and not restrictive.

I. Overview of Exemplary Circular Stapling Surgical Instrument

Figure 2:
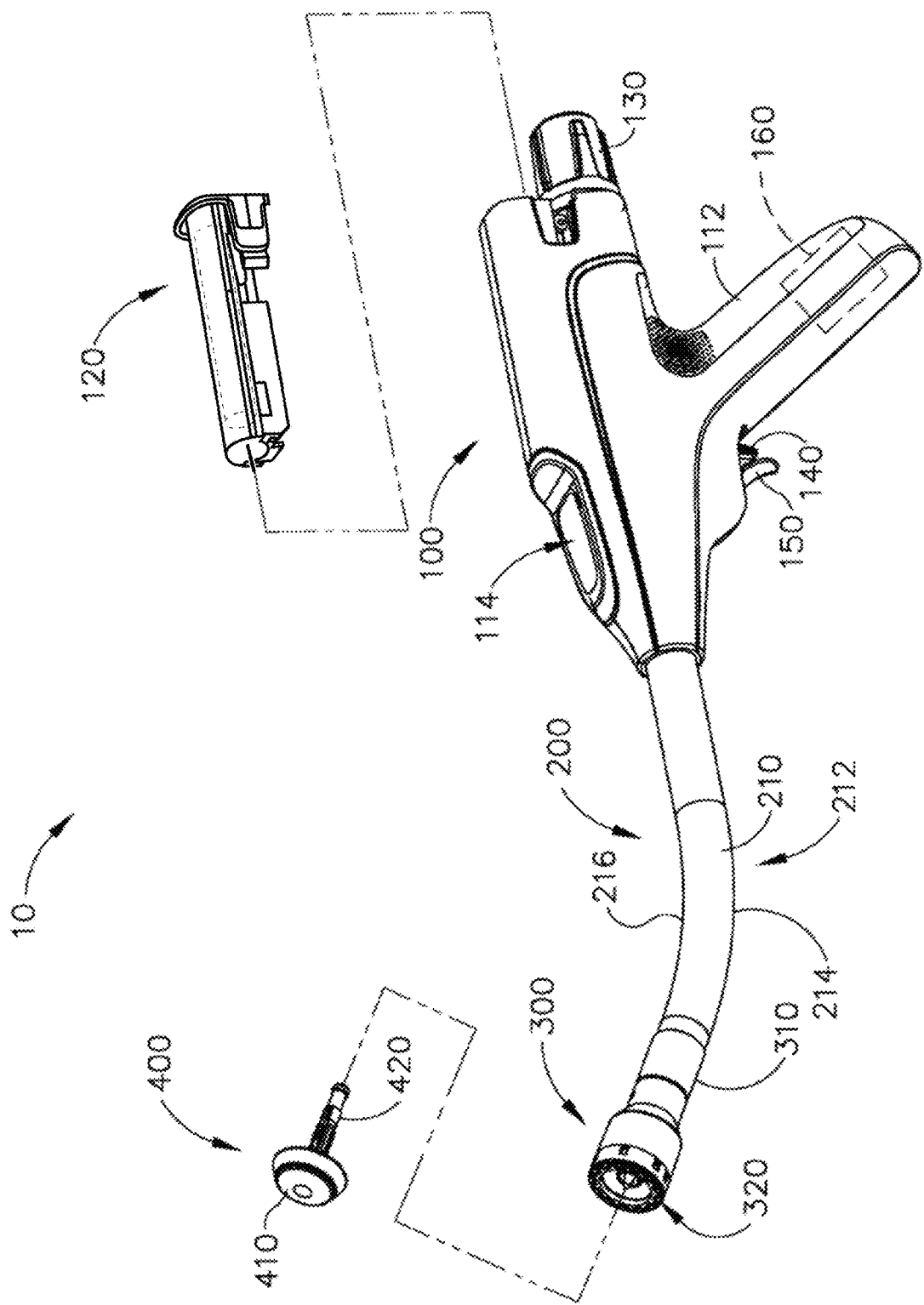
FIG. 2 depicts a perspective view of the circular stapler of FIG. 1, with a battery pack removed from a handle assembly and an anvil removed from a stapling head assembly, according to one aspect of the present disclosure.

FIGS. 1 and 2 depict an exemplary surgical circular stapler (10) that may be used to provide an end-to-end anastomosis between two sections of an anatomical lumen such as a portion of a patient's digestive tract. Circular stapler (10) of this example comprises a handle assembly (100), a shaft assembly (200), a stapling head assembly (300), an anvil (400), and a removable battery pack (120). Each of these components will be described in greater detail below.

A. Exemplary Tissue Engagement Features of Circular Stapling Instrument

Figure 3:
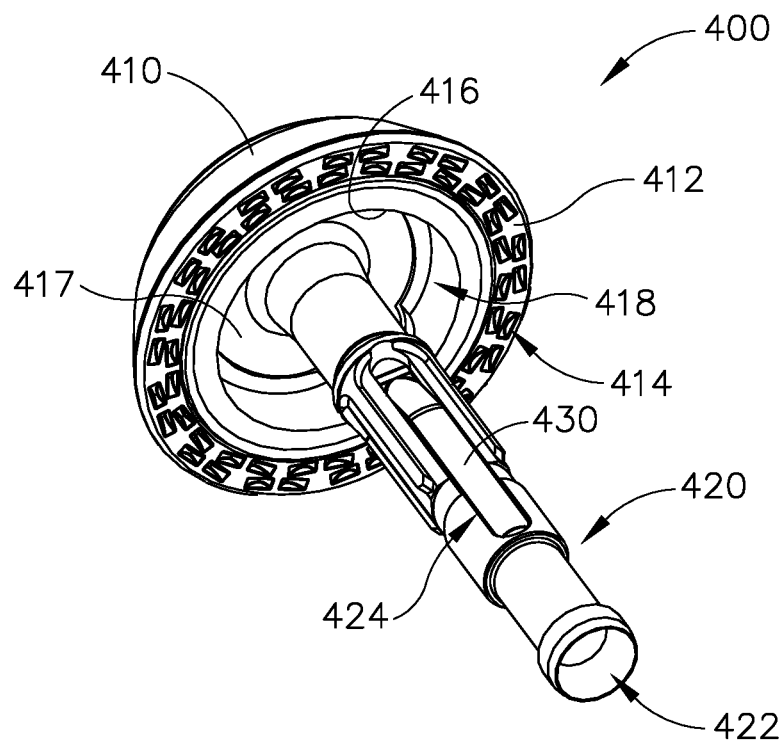
FIG. 3 depicts a perspective view of the anvil of the circular stapler of FIG. 1, according to one aspect of the present disclosure.

As best seen in FIG. 3, anvil (400) of the present example comprises a head (410) and a shank (420). Head (410) includes a proximal surface (412) that defines a plurality of staple forming pockets (414). Staple forming pockets (414) are arranged in two concentric annular arrays in the present example. Staple forming pockets (414) are configured to deform staples as the staples are driven into staple forming pockets (414) (e.g., deforming a generally "U" shaped staple into a "B" shape as is known in the art). Shank (420) defines a bore or lumen (422) and includes a pair of pivoting latch members (430) positioned in bore (422). Each latch member (430) includes features that allows anvil (400) to be removably secured to a trocar (330) of stapling head assembly (300) as will be described in greater detail below. It should be understood, however, that anvil (400) may be removably secured to a trocar (330) using any other suitable components, features, or techniques.

Figure 4:
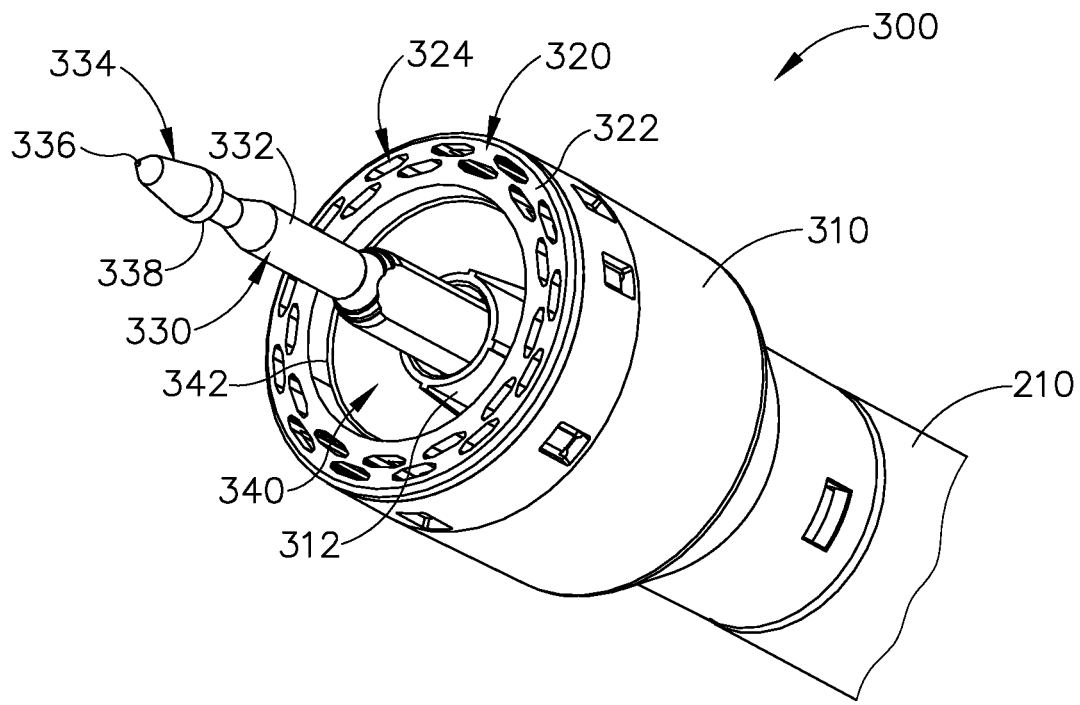
FIG. 4 depicts a perspective view of the stapling head assembly of the circular stapler of FIG. 1, according to one aspect of the present disclosure.
Figure 5:
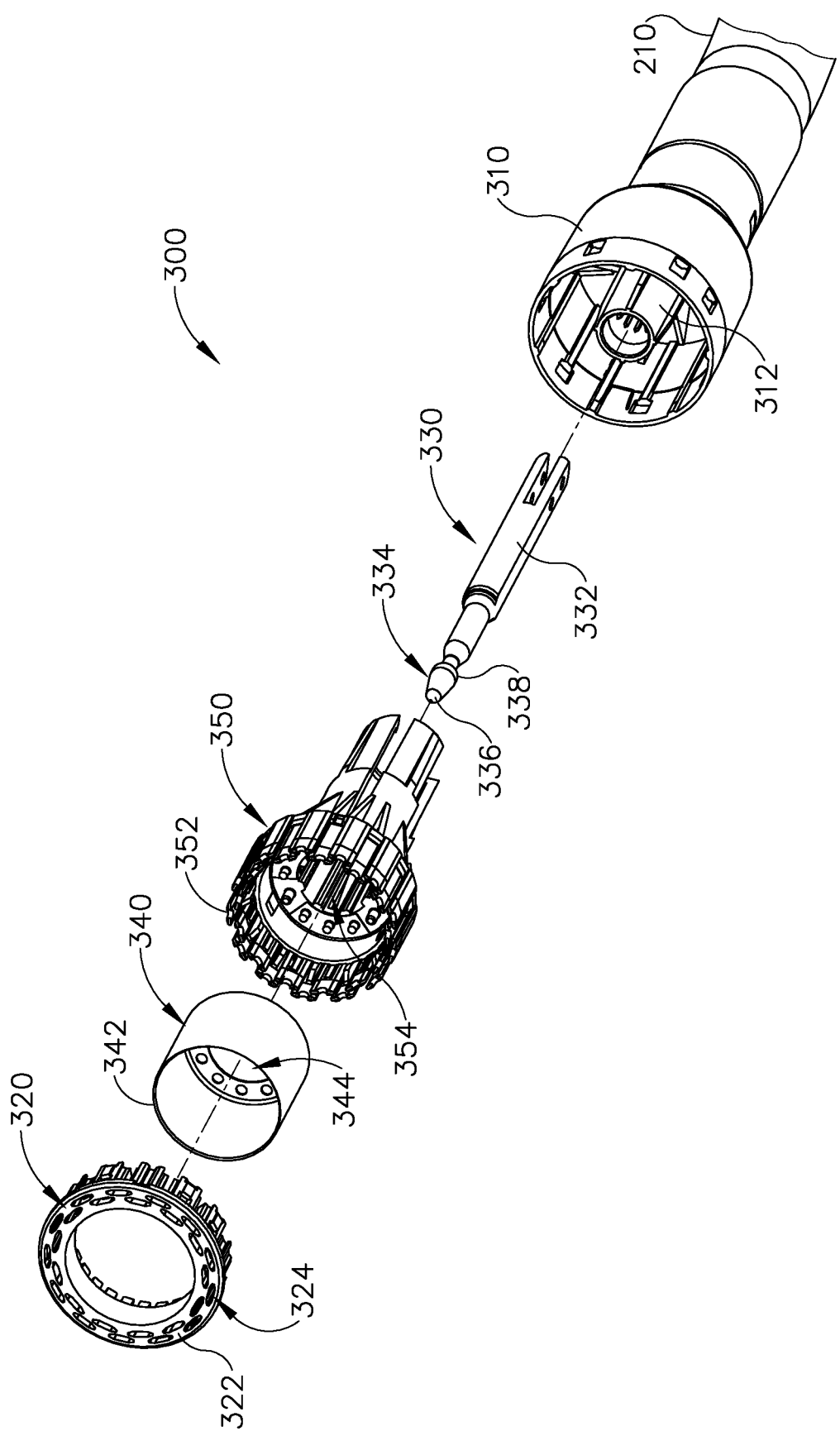
FIG. 5 depicts an exploded perspective view of the stapling head assembly of FIG. 4, according to one aspect of the present disclosure.

Stapling head assembly (300) is located at the distal end of shaft assembly (200). As shown in FIGS. 1 and 2, anvil (400) is configured to removably couple with shaft assembly (200), adjacent to stapling head assembly (300). As will be described in greater detail below, anvil (400) and stapling head assembly (300) are configured to cooperate to manipulate tissue in three ways, including clamping the tissue, cutting the tissue, and stapling the tissue. As best seen in FIGS. 4 and 5, stapling head assembly (300) of the present example comprises a tubular casing (310) housing a slidable staple driver member (350). A cylindraceous inner core member (312) extends distally within tubular casing (310). Tubular casing (310) is fixedly secured to an outer sheath (210) of shaft assembly (200), such that tubular casing (310) serves as a mechanical ground for stapling head assembly (300).

Trocar (330) is positioned coaxially within inner core member (312) of tubular casing (310). Trocar (330) is operable to translate distally and proximally relative to tubular casing (310) in response to rotation of a knob (130) located at the proximal end of handle assembly (100). Trocar (330) comprises a shaft (332) and a head (334). Head (334) includes a pointed tip (336) and an inwardly extending proximal surface (338). Head (334) and the distal portion of shaft (332) are configured for insertion in bore (422) of anvil (400). Proximal surface (338) is configured to complement features of latch members (430) to provide a snap fit between anvil (400) and trocar (330).

Staple driver member (350) is operable to actuate longitudinally within tubular casing (310) in response to activation of motor (160) as will be described in greater detail below. Staple driver member (350) includes two distally presented concentric annular arrays of staple drivers (352). Staple drivers (352) are arranged to correspond with the arrangement of staple forming pockets (414) described above. Thus, each staple driver (352) is configured to drive a corresponding staple into a corresponding staple forming pocket (414) when stapling head assembly (300) is actuated. Staple driver member (350) also defines a bore (354) that is configured to coaxially receive core member (312) of tubular casing (310).

A cylindraceous knife member (340) is coaxially positioned within staple driver member (350). Knife member (340) includes a distally presented, sharp circular cutting edge (342). Knife member (340) is sized such that knife member (340) defines an outer diameter that is smaller than the diameter defined by the inner annular array of staple drivers (352). Knife member (340) also defines an opening that is configured to coaxially receive core member (312) of tubular casing (310).

A deck member (320) is fixedly secured to tubular casing (310). Deck member (320) includes a distally presented deck surface (322) defining two concentric annular arrays of staple openings (324). Staple openings (324) are arranged to correspond with the arrangement of staple drivers (352) and staple forming pockets (414) described above. Thus, each staple opening (324) is configured to provide a path for a corresponding staple driver (352) to drive a corresponding staple through deck member (320) and into a corresponding staple forming pocket (414) when stapling head assembly (300) is actuated. It should be understood that the arrangement of staple openings (324) may be modified just like the arrangement of staple forming pockets (414) as described above. It should also be understood that various structures and techniques may be used to contain staples within stapling head assembly (300) before stapling head assembly (300) is actuated. Deck member (320) defines an inner diameter that is just slightly larger than the outer diameter defined by knife member (340). Deck member (320) is thus configured to allow knife member (340) to translate distally to a point where cutting edge (342) is distal to deck surface (322).

Figure 6:
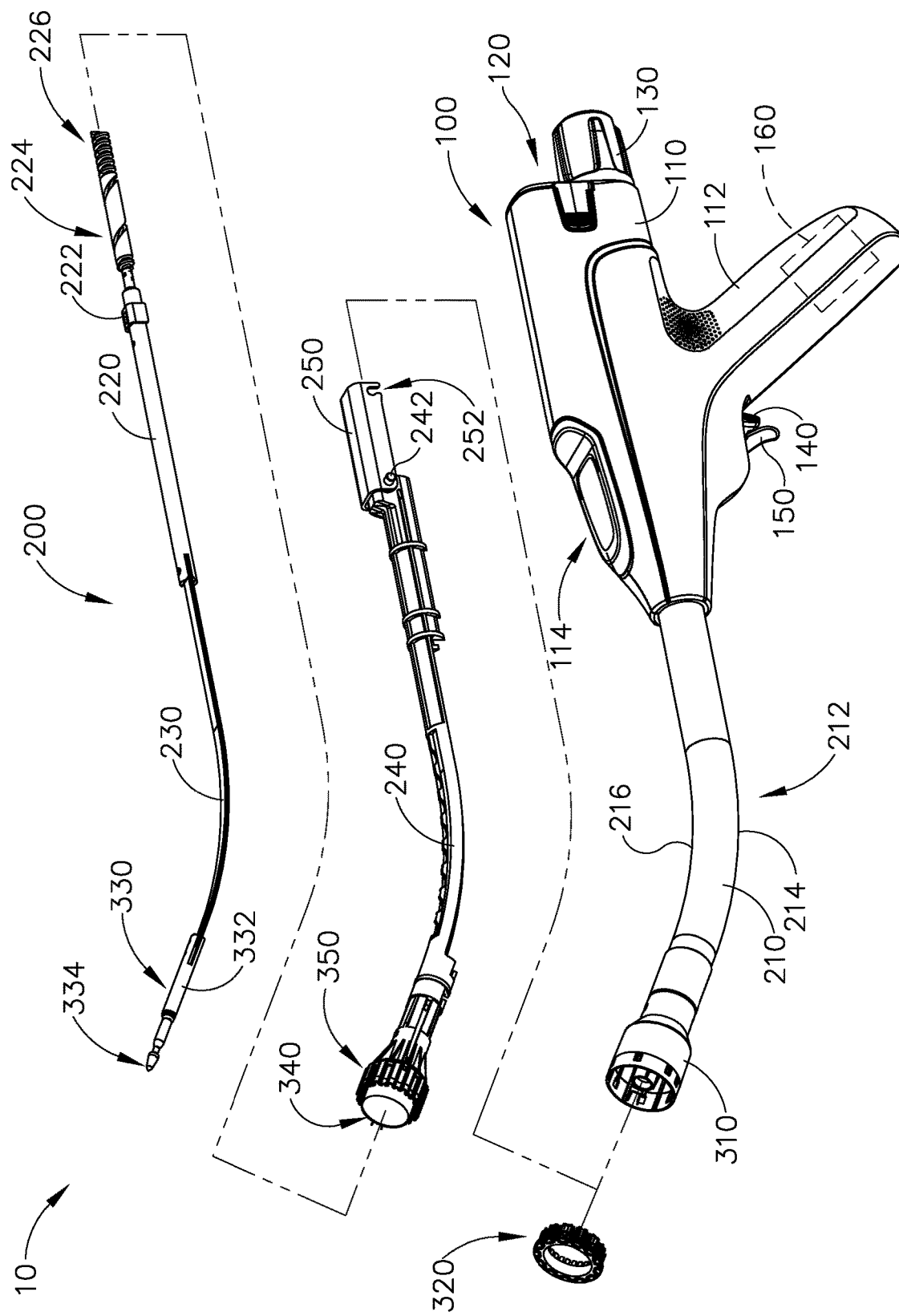
FIG. 6 depicts an exploded perspective view of the circular stapler of FIG. 1, with portions of the shaft assembly shown separately from each other, according to one aspect of the present disclosure.

FIG. 6 shows various components of shaft assembly (200), which extends distally from handle assembly (100) and couples components of stapling head assembly (300) with components of handle assembly (100). In particular, and as noted above, shaft assembly (200) includes an outer sheath (210) that extends between handle assembly (100) and tubular casing (310). In the present example, outer sheath (210) is rigid and includes a preformed curved section (212) that is configured to facilitate positioning of stapling head assembly (300) within a patient's colon as described below. Curved section (212) includes an inner curve (216) and an outer curve (214).

Shaft assembly (200) further includes a trocar actuation rod (220) and a trocar actuation band assembly (230). The distal end of trocar actuation band assembly (230) is fixedly secured to the proximal end of trocar shaft (332). The proximal end of trocar actuation band assembly (230) is fixedly secured to the distal end of trocar actuation rod (220), such that trocar (330) will translate longitudinally relative to outer sheath (210) in response to translation of trocar actuation band assembly (230) and trocar actuation rod (220) relative to outer sheath (210). Trocar actuation band assembly (230) is configured to flex such that trocar actuation band assembly (230) may follow along the preformed curve in shaft assembly (200) as trocar actuation band assembly (230) is translated longitudinally relative to outer sheath (210). However, trocar actuation band assembly (230) has sufficient column strength and tensile strength to transfer distal and proximal forces from trocar actuation rod (220) to trocar shaft (332). Trocar actuation rod (220) is rigid. A clip (222) is fixedly secured to trocar actuation rod (220) and is configured to cooperate with complementary features within handle assembly (100) to prevent trocar actuation rod (220) from rotating within handle assembly (100) while still permitting trocar actuation rod (220) to translate longitudinally within handle assembly (100). Trocar actuation rod (220) further includes a coarse helical threading (224) and a fine helical threading (226).

Shaft assembly (200) further includes a stapling head assembly driver (240) that is slidably received within outer sheath (210). The distal end of stapling head assembly driver (240) is fixedly secured to the proximal end of staple driver member (350). The proximal end of stapling head assembly driver (240) is secured to a drive bracket (250) via a pin (242). It should therefore be understood that staple driver member (350) will translate longitudinally relative to outer sheath (210) in response to translation of stapling head assembly driver (240) and drive bracket (250) relative to outer sheath (210). Stapling head assembly driver (240) is configured to flex such that stapling head assembly driver (240) may follow along the preformed curve in shaft assembly (200) as stapling head assembly driver (240) is translated longitudinally relative to outer sheath (210). However, stapling head assembly driver (240) has sufficient column strength to transfer distal forces from drive bracket (250) to staple driver member (350).

B. Exemplary User Input Features of Circular Stapling Instrument

As shown in FIG. 1, handle assembly (100) includes a pistol grip (112) and several components that are operable to actuate anvil (400) and stapling head assembly (300). In particular, handle assembly (100) includes knob (130), a safety trigger (140) a firing trigger (150), a motor (160), and a motor activation module (180). Knob (130) is coupled with trocar actuation rod (220) via a nut (not shown), such that coarse helical threading (224) will selectively engage a thread engagement feature within the interior of the nut; and such that fine helical threading (226) will selectively engage a thread engagement feature within the interior of knob (130). These complementary structures are configured such that trocar actuation rod (220) will first translate proximally at a relatively slow rate, then translate proximally at a relatively fast rate, in response to rotation of knob (130).

It should be understood that when anvil (400) is coupled with trocar (330), rotation of knob (130) will provide corresponding translation of anvil relative to stapling head assembly (300). It should also be understood that knob (130) may be rotated in a first angular direction (e.g., clockwise) to retract anvil (400) toward stapling head assembly (300); and in a second angular direction (e.g., counterclockwise) to advance anvil (400) away from stapling head assembly (300). Knob (130) may thus be used to adjust the gap distance between opposing surfaces (412, 322) of anvil (400) and stapling head assembly (300) until a suitable gap distance has been achieved.

In the present example, handle assembly (100) comprises a user feedback feature (114) that is configured to provide the operator with visual feedback indicating the positioning of anvil (400) in relation to stapling head assembly (300). The operator may thus observe user feedback feature (114) while rotating knob (130), to confirm whether the suitable gap distance between anvil (400) and stapling head assembly (300) has been achieved.

Firing trigger (150) is operable to activate motor (160) to thereby actuate stapling head assembly (300). Safety trigger (140) is operable to selectively block actuation of firing trigger (150) based on the longitudinal position of anvil (400) in relation to stapling head assembly (300). Handle assembly (100) also includes components that are operable to selectively lock out both triggers (140, 150) based on the position of anvil (400) relative to stapling head assembly (300). When triggers (140, 150) are locked out, firing trigger (150) is prevented from initiating actuation of stapling head assembly (300). Thus, trigger (150) is only operable to initiate actuation of stapling head assembly (300) when the position of anvil (400) relative to stapling head assembly (300) is within a predefined range.

In the present example, firing trigger (150) of the present example includes an integral actuation paddle. The paddle is configured to actuate a switch of motor activation module (180) (FIG. 1) when firing trigger (150) is pivoted to a fired position. Motor activation module (180) is in communication with battery pack (120) and motor (160), such that motor activation module (180) is configured to provide activation of motor (160) with electrical power from battery pack (120) in response to the paddle actuating the switch of motor activation module (180). Thus, motor (160) will be activated when firing trigger (150) is pivoted. This activation of motor (160) will actuate stapling head assembly (300) as described in greater detail below.

Battery pack (120) is operable to provide electrical power to a motor (160) as noted above. Battery pack (120) may be removably coupled with handle assembly (100) through a snap fit or in any other suitable fashion. It should be understood that battery pack (120) and handle assembly (100) may have complementary electrical contacts, pins and sockets, and/or other features that provide paths for electrical communication from battery pack (120) to electrically powered components in handle assembly (100) when battery pack (120) is coupled with handle assembly (100). It should also be understood that, in some versions, battery pack (120) is unitarily incorporated within handle assembly (100) such that battery pack (120) cannot be removed from handle assembly (100). As will be discussed in greater detail below, battery pack (120) can consist of battery (122) and battery housing (608). The battery housing (608) can be the outer shell of the battery pack (120) that connects to or otherwise engages with handle assembly (see, e.g., FIG. 8). The battery pack (120) can be inserted into housing cavity (610) within handle assembly (100).

C. Exemplary Anastomosis Procedure with Circular Stapling Instrument

FIGS. 7A-7E show circular stapler (10) being used to form an anastomosis (70) between two tubular anatomical structures (20, 40). By way of example only, the tubular anatomical structures (20, 40) may comprise sections of a patient's esophagus, sections of a patient's colon, other sections of the patient's digestive tract, or any other tubular anatomical structures. In some versions, one or more diseased portions of a patient's colon are removed, with the tubular anatomical structures (20, 40) of FIGS. 7A-7E representing the remaining severed portions of the colon.

Figure 7A:
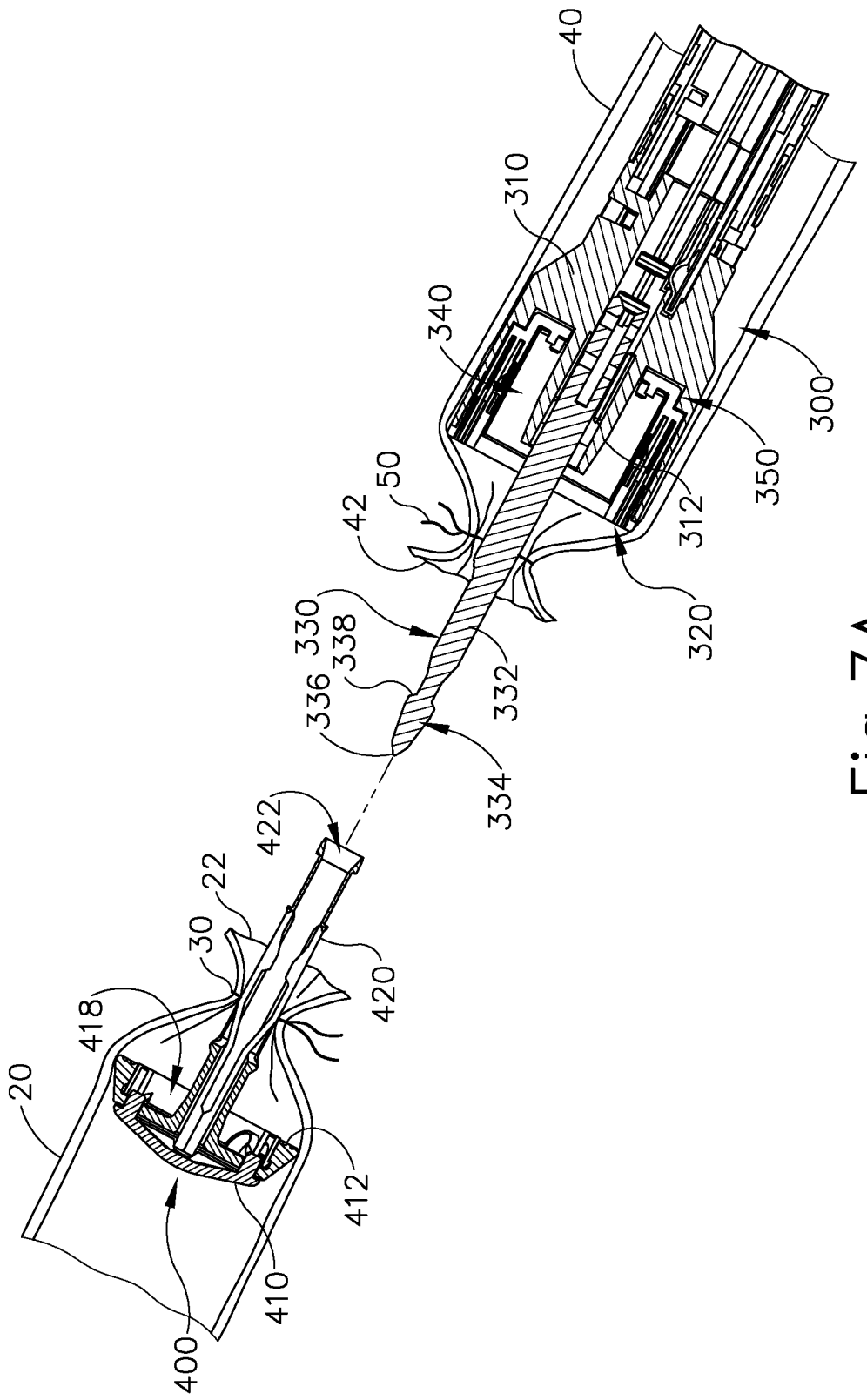
FIG. 7A depicts a cross-sectional side view of the anvil of FIG. 3 positioned within a first section of a digestive tract and the stapling head assembly of FIG. 4 positioned in a second section of the digestive tract, with the anvil separated from the stapling head assembly, according to one aspect of the present disclosure.

As shown in FIG. 7A, anvil (400) is positioned in one tubular anatomical structure (20) and stapling head assembly (300) is positioned in another tubular anatomical structure (40). In versions where tubular anatomical structures (20, 40) comprise sections of a patient's colon, stapling head assembly (300) may be inserted via the patient's rectum. It should also be understood that the procedure depicted in FIGS. 7A-7E is an open surgical procedure, though the procedure may instead be performed laparoscopically. By way of example only, the surgical procedure may be performed laparoscopically. Various other suitable ways in which circular stapler (10) may be used to form an anastomosis (70) in a laparoscopic procedure will be apparent to those of ordinary skill in the art in view of the teachings herein.

As shown in FIG. 7A, anvil (400) is positioned in tubular anatomical structure (20) such that shank (420) protrudes from the open severed end (22) of tubular anatomical structure (20). A purse-string suture (30) is provided about a mid-region of shank (420) to generally secure the position of anvil (400) in tubular anatomical structure (20). Similarly, stapling head assembly (300) is positioned in tubular anatomical structure (40) such that trocar (330) protrudes from the open severed end (42) of tubular anatomical structure (20). A purse-string suture (50) is provided about a mid-region of shaft (332) to generally secure the position of stapling head assembly (300) in tubular anatomical structure (40).

Figure 7B:
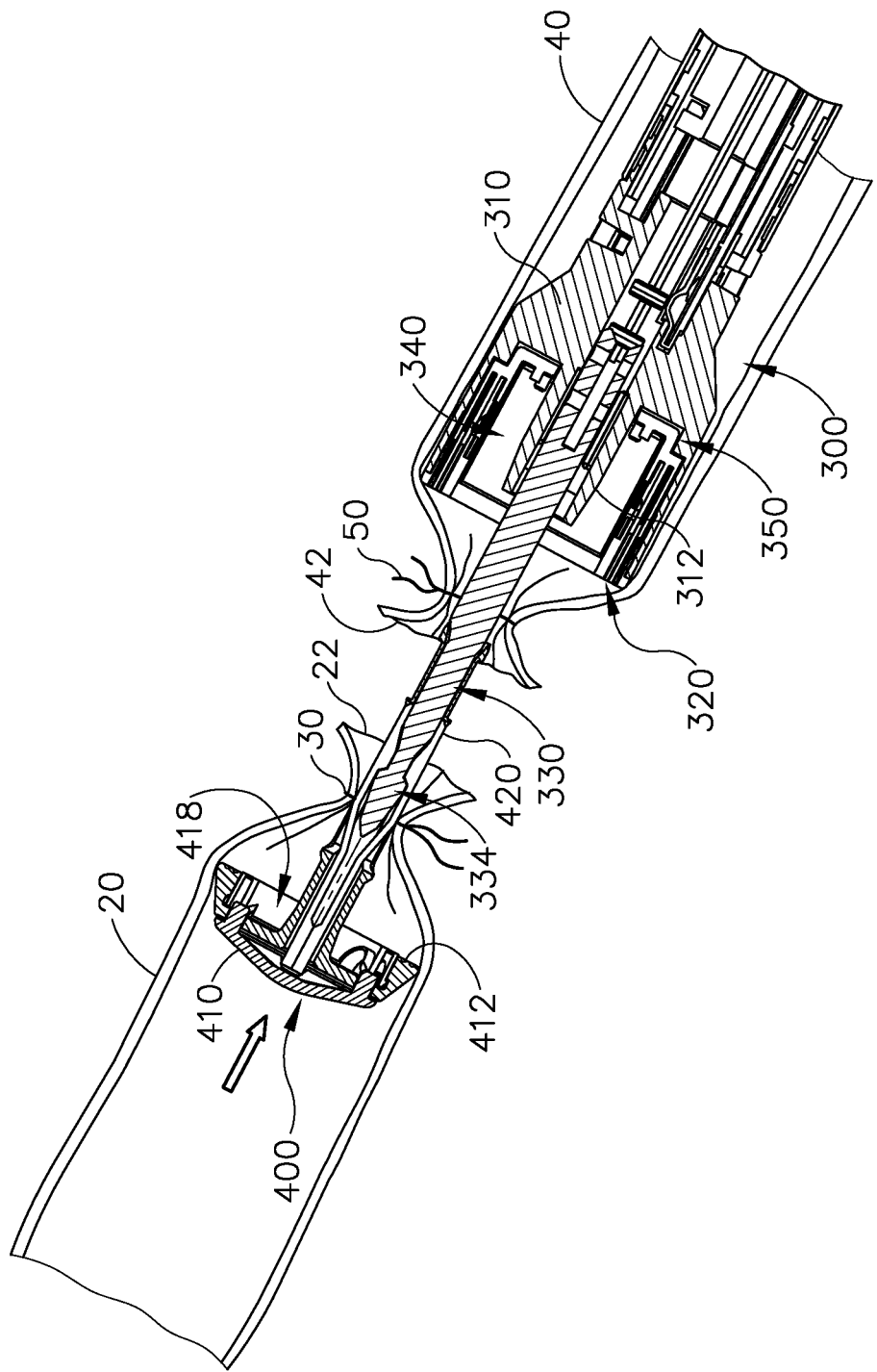
FIG. 7B depicts a cross-sectional side view of the anvil of FIG. 3 positioned within the first section of the digestive tract and the stapling head assembly of FIG. 4 positioned in the second section of the digestive tract, with the anvil secured to the stapling head assembly, according to one aspect of the present disclosure.
Figure 7C:
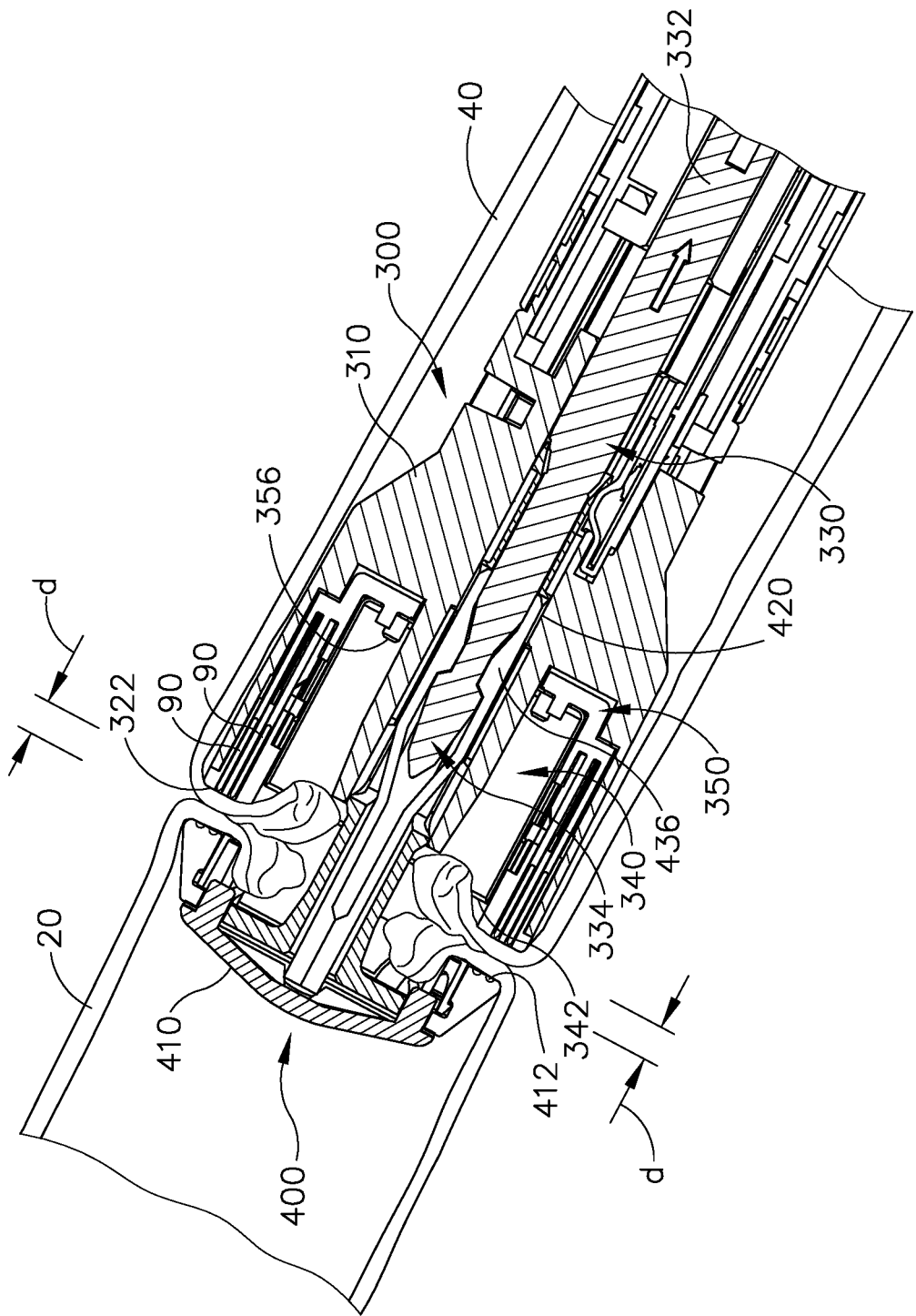
FIG. 7C depicts a cross-sectional side view of the anvil of FIG. 3 positioned within the first section of the digestive tract and the stapling head assembly of FIG. 4 positioned in the second section of the digestive tract, with the anvil retracted toward the stapling head assembly to thereby clamp tissue between the anvil and the stapling head assembly, according to one aspect of the present disclosure.

Next, anvil (400) is secured to trocar (330) by inserting trocar (330) into bore (422) as shown in FIG. 7B. Latch members (430) engage head (334) of trocar (330), thereby providing a secure fit between anvil (400) and trocar (330). The operator then rotates knob (130) while holding handle assembly (100) stationary via pistol grip (112). This rotation of knob (130) causes trocar (330) and anvil (400) to retract proximally, as described above. As shown in FIG. 7C, this proximal retraction of trocar (330) and anvil (400) compresses the tissue of tubular anatomical structures (20, 40) between surfaces (412, 322) of anvil (400) and stapling head assembly (300). The operator observes user feedback feature (114) to determine whether the gap distance (d) between opposing surfaces (412, 322) of anvil (400) and stapling head assembly (300) is appropriate; and makes any necessary adjustments via knob (130).

Figure 7D:
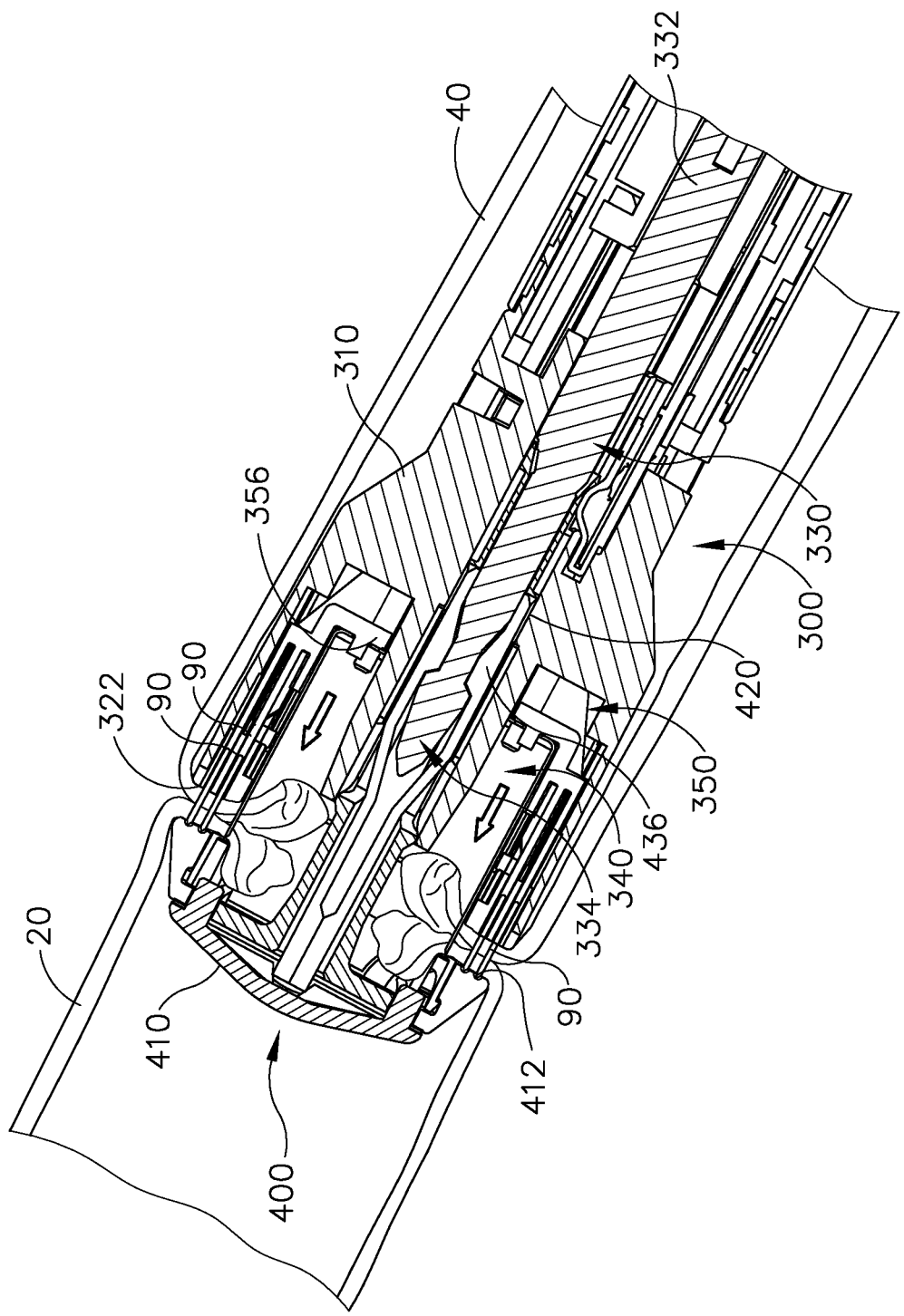
FIG. 7D depicts a cross-sectional side view of the anvil of FIG. 3 positioned within the first section of the digestive tract and the stapling head assembly of FIG. 4 positioned in the second section of the digestive tract, with the stapling head assembly actuated to sever and staple the clamped tissue, according to one aspect of the present disclosure.

Once the operator has appropriately set the gap distance (d) via knob (130), the operator actuates safety trigger (140) to enable actuation of firing trigger (150). The operator then actuates firing trigger (150). This actuation of firing trigger (150) in turn actuates a switch of motor activation module (180), which in turn activates motor (160) to thereby actuate stapling head assembly (300) by driving knife member (340) and staple driver member (350) distally as shown in FIG. 7D. As knife member (340) translates distally, cutting edge (342) of knife member (340) cooperates with inner edge (416) of anvil (400), thereby shearing excess tissue that is positioned within annular recess (418) of anvil (400) and the interior of knife member (340).

As shown in FIG. 4, anvil (400) of the present example includes a breakable washer (417) within annular recess (418). This washer (417) is broken by knife member (340) when knife member (340) completes a full distal range of motion from the position shown in FIG. 7C to the position shown in FIG. 7D. The drive mechanism for knife member (340) may provide an increasing mechanical advantage as knife member (340) reaches the end of its distal movement, thereby providing greater force by which to break washer (417). Of course, breakable washer (417) may be omitted entirely in some versions. In versions where washer (417) is included, it should be understood that washer (417) may also serve as a cutting board for knife member (340) to assist in cutting of tissue. Such a cutting technique may be employed in addition to or in lieu of the above-noted shearing action between inner edge (416) and cutting edge (342).

As staple driver member (350) translates distally from the position shown in FIG. 7C to the position shown in FIG. 7D, staple driver member (350) drives staples (90) through the tissue of tubular anatomical structures (20, 40) and into staple forming pockets (414) of anvil (400). Staple forming pockets (414) deform the driven staples (90) into a "B" shape as is known in the art. The formed staples (90) thus secure the ends of tissue together, thereby coupling tubular anatomical structure (20) with tubular anatomical structure (40).

After the operator has actuated stapling head assembly (300) as shown in FIG. 7D, the operator rotates knob (130) to drive anvil (400) distally away from stapling head assembly (300), increasing the gap distance (d) to facilitate release of the tissue between surfaces (412, 322). The operator then removes circular stapler (10) from the patient, with anvil (400) still secured to trocar (330). Referring back to the example where the tubular anatomical structures (20, 40) comprise sections of a patient's colon, circular stapler (10) may be removed via the patient's rectum. With circular stapler (10) removed, the tubular anatomical structures (20, 40) are left secured together by two annular arrays of staples (90) at an anastomosis (70) as shown in FIG. 7E. The inner diameter of the anastomosis (70) is defined by the severed edge (60) left by knife member (340).

In some instances, it may be desirable to change the configuration and arrangement of staple forming pockets (414) in anvil (400). It should be understood that reconfiguring and rearranging staple forming pockets (414) may result in reconfiguration and rearrangement of staples (90) that are formed by staple forming pockets (414). For instance, the configuration and arrangement of staple forming pockets (414) may affect the structural integrity of an anastomosis (70) that is secured by staples (90). In addition, the configuration and arrangement of staple forming pockets (414) may affect the hemostasis that is achieved at an anastomosis (70) that is secured by staples (90). The following description relates to several exemplary variations of anvil (400), providing staple forming pocket configurations and arrangements that differ from those of staple forming pockets (414).

It should be understood that the various alternatives to anvil (400) described below may be readily used with circular stapler (10), in place of anvil (400). It should also be understood that, in some instances, the configuration and arrangement of staple openings (324) in deck member (320) may need to be varied in order to complement the configuration and arrangement of the alternative staple forming pockets described below. Various suitable ways in which the alternatives to anvil (400) described below may be incorporated into circular stapler (10) will be apparent to those of ordinary skill in the art in view of the teachings herein.

Circular stapler (10) described herein can include smart components that generate data and transmit the data to other remote components. In one example, circular stapler (10) can include a smart anvil (400), as will be described in greater detail with respect to FIG. 17. The anvil (400) can generate signals inside of an operative site, for example data about the location of the anvil (400) (e.g., whether or not anvil (400) is current attached to stapling head assembly (300)) and/or information about the firing of the staples (90), such as the force seen on anvil (400) during the firing process. The anvil (400) can transmit data about those signals to outside of the patient. One issue with this, however, is that many wireless frequencies and protocols, such as Wi-Fi™ and Bluetooth™ are susceptible to interference from human tissue, and as such location of an antenna both inside the patient and outside the patient is important. FIGS. 8-13B each provide example locations of an antenna or transceiver (e.g., handle transceiver (604)) within a handle assembly (100) that enables signals to be sent close range (yet through tissue) to handle assembly, then long range to an external hub (902) outside of the patient. Additional information about circular staplers can be found in U.S. Publication No. 2018/0132849, entitled Staple Forming Pocket Configurations For Circular Surgical Stapler Anvil, which is incorporated herein by reference in its entirety.

Figure 8:
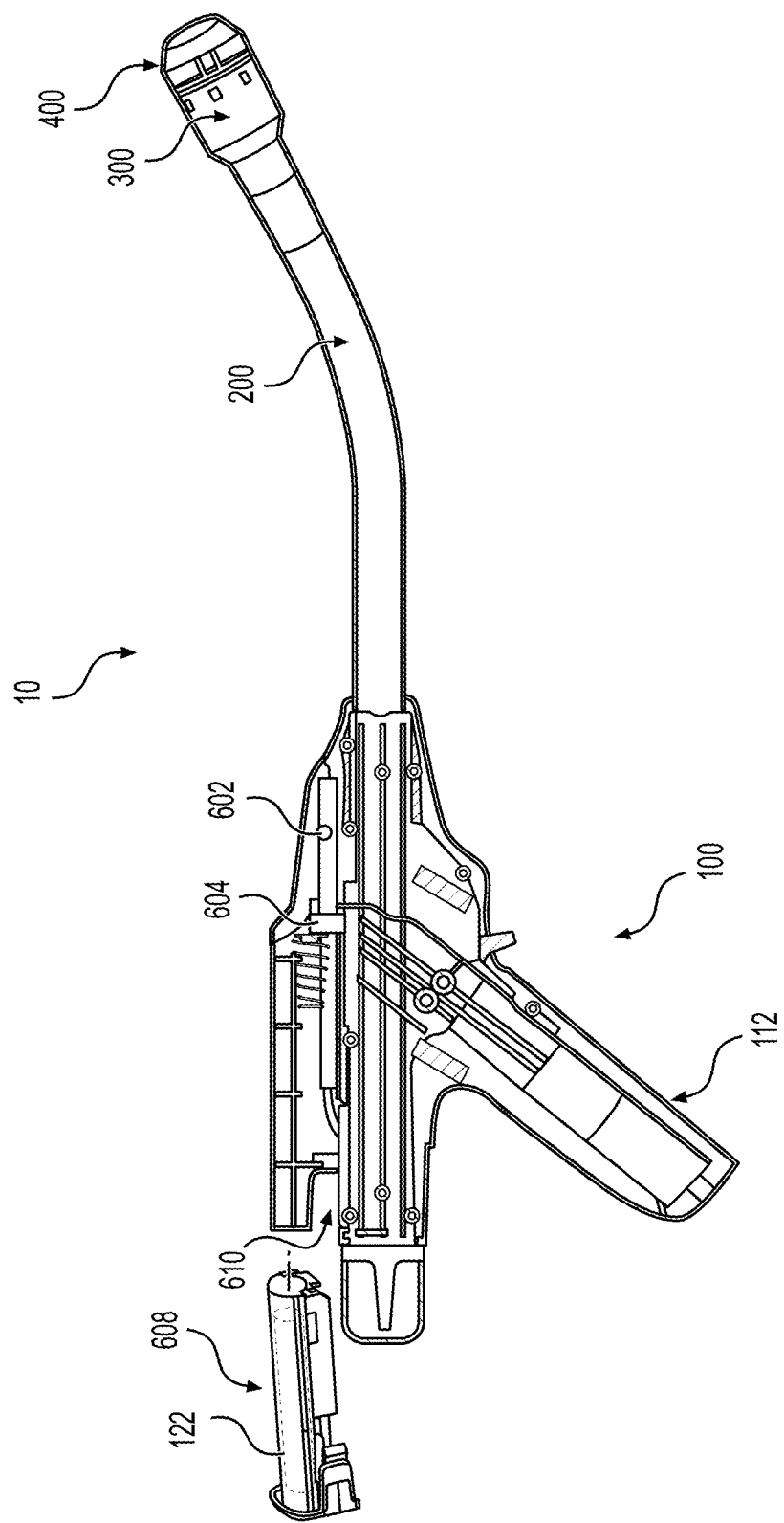
FIG. 8 depicts a circular stapler with a handle transceiver positioned proximate a handle controller, according to one aspect of the present disclosure.

Referring now to FIG. 8, the example depicts a circular stapler (10) with a handle transceiver (604) positioned proximate a handle controller (602), according to one aspect of the present disclosure. Additional information about handle controller (602) is provided below with respect to FIG. 17. In general, handle controller (602) can include hardware and/or software to help control (i.e., generate or receive firing signals to and from stapling head assembly (300) or other components of the circular stapler (10) such as the motor (160)) or monitor the device (i.e., generate or receive information about previous staple firings for the device). Referring briefly to FIG. 18 for illustration, anvil (400) during operation is positioned inside an obstruction (900) (e.g., the patient's abdomen). Anvil (400) can generate said information about the stapling procedure at the distal end of the device within obstruction (900), and relay that information outside of obstruction (900). An implementation can be to send that information to external hub (902), which can include an external computing system with a display for providing the information received from within obstruction (900). That external hub (902) can be positioned many feet away from the location of circular stapler (10), and since the patient's tissue can obstruct signals in the normal range of operation of such devices (e.g., around 2.4 GHz for Bluetooth™ or Wi-Fi™), the obstruction may be such that the signals cannot reach hub (902). This is further exacerbated by the fact circular staplers (10) have detachably attachable anvils, unlike what is found in linear staplers, and as such anvil (400) can continuously change positions (and distance) from handle assembly (100). In the present disclosure, handle transceiver (604) can act as a relay to both (i) receive short-range signals from anvil transceiver (706) and (ii) transmit longer-range signals to hub (902). An improvement in the present design is that the relay (i.e., handle transceiver (604)) is positioned as close to the distal component (anvil transceiver (706)) as physically possible—i.e., handle transceiver (604) is placed in handle assembly. Another inventive aspect of the disclosure, therefore, is that the designs herein (see FIGS. 8-13B) each provide solutions in their own right to improve the wireless connection between handle transceiver (604) and anvil transceiver (706)).

Referring again to handle controller (602), in any embodiment described herein, the controller can be positioned within handle assembly (100). As shown in FIG. 8, handle controller (602) is positioned proximate housing cavity (610) that accepts battery housing (608). Positioning handle controller (602) within handle assembly (100) near the location of battery (122) within battery housing (608) can help to ensure a secure, solid, and direct connection to that power source. Further, and as described below with reference to FIGS. 13A and 13B, handle assembly (100) can also include display panel (618) including a display (620), and positioning handle controller (602) on the upper portion of handle assembly (100) enables handle controller (602) to be positioned proximate display panel (618). As described above, one aspect of the present disclosure is to provide a means of communication between handle assembly (100) and anvil (400). As such, handle assembly (100) acts to receive the signals from anvil (400). As shown, handle transceiver (604) is positioned close to handle controller (602) to provide a short connection to the controller, and in some instances handle transceiver (604) can be positioned on the same circuit board that comprises handle controller (602). The location of handle transceiver (604) in FIG. 8 allows for the transceiver to be positioned on the upper part of handle assembly (100) such that the transceiver has a clear and direct path to anvil (400) positioned within the patient. As discussed above, shaft assembly (200) can include preformed curved section (212) that is configured to facilitate positioning of stapling head assembly (300) within the patient's colon, and the curve can help to further align anvil (400) in a direct path, less obstructed to handle transceiver (604).

Figure 9:
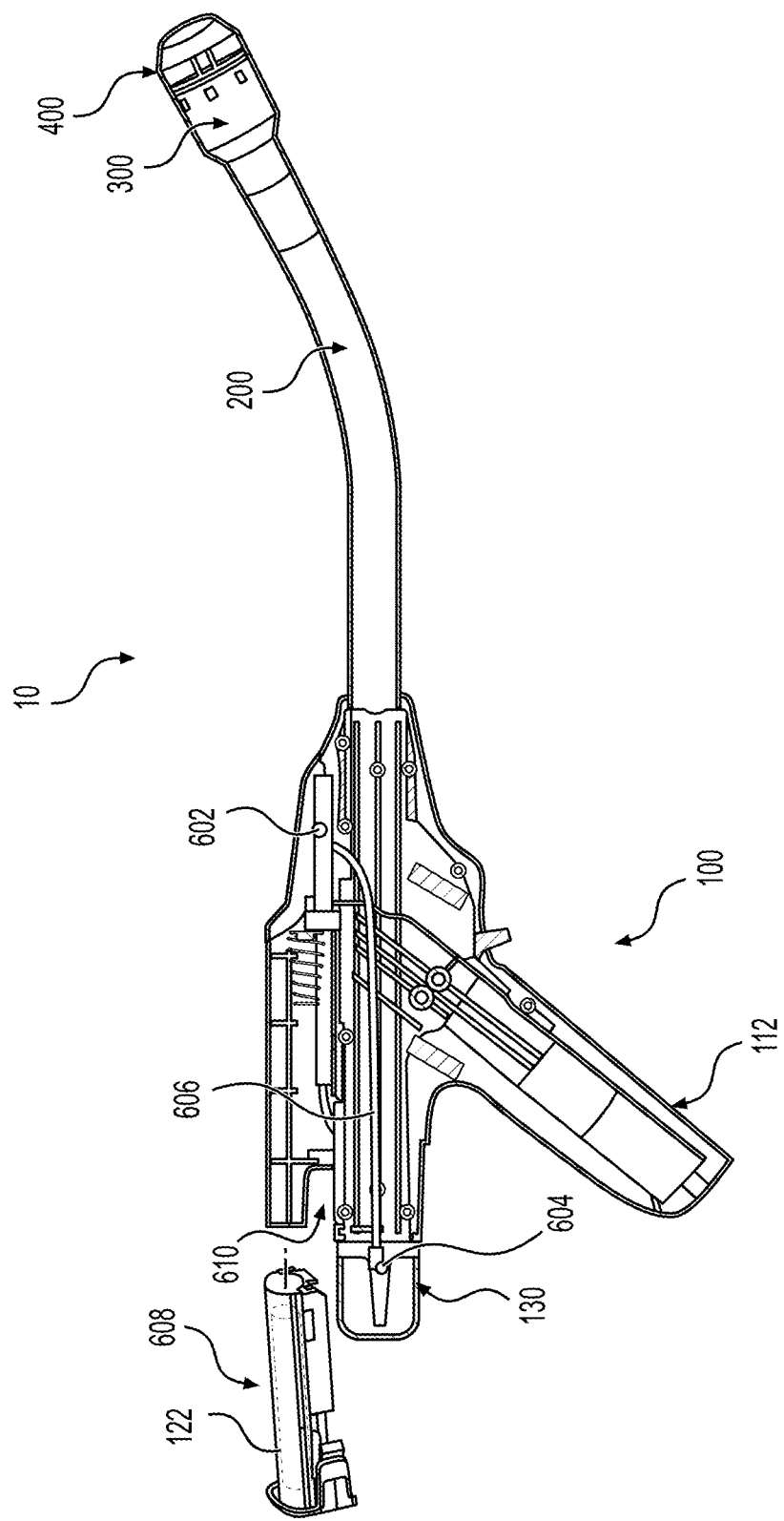
FIG. 9 depicts a circular stapler with a handle transceiver positioned within a proximal knob, according to one aspect of the present disclosure.

FIG. 9 depicts circular stapler (10) with handle transceiver (604) positioned within a proximal knob (130), according to one aspect of the present disclosure. Knob (130) is located at the proximal end of handle assembly (100) and is the most distant part of handle assembly (100) from the patient during operation. As such, knob (130) provides a preferred location for handle transceiver (604). The handle (e.g., pistol grip (112)) and the knob (130) are both surgeon (or surgical staff) used components. As a result, the components are located exterior to the patient (obstruction (900)) and as a result would be an effective relay location, as they can be guaranteed to have minimal obstructions present. At this location, however, handle transceiver (604) is positioned within handle assembly (100) distal to handle controller (602). As such, handle transceiver (604) cannot then be positioned on the same circuit board as handle controller (602), and the communication between the two components can be completed by use of connector (606). This connector (606) can be a coaxial cable or the like that enables handle transceiver (604) to be positioned within the center of knob (130) such that knob (130) is able to freely rotate around handle controller (602) itself.

Figure 10:
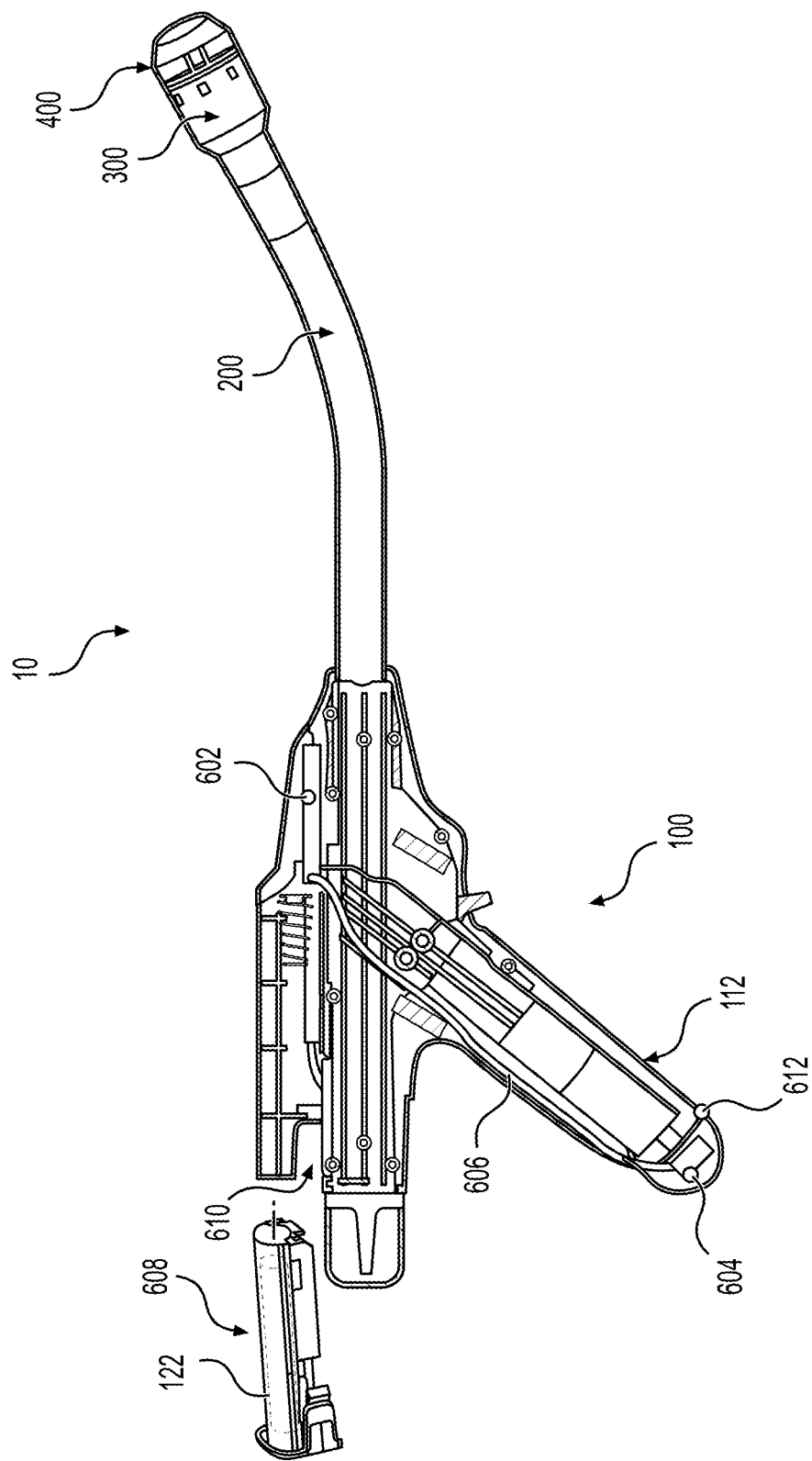
FIG. 10 depicts a circular stapler with a handle transceiver positioned within a pistol grip, according to one aspect of the present disclosure.

FIG. 10 depicts circular stapler (10) with handle transceiver (604) positioned within pistol grip (112), according to one aspect of the present disclosure. As described above, handle assembly (100) can include several electrical components, such as handle controller (602) and motor (160). These components, and particularly motor (160), can create electrical noise during operation, and as such the signal being sent from anvil (400) to handle transceiver (604) can be degraded by the radiofrequency interference. Pistol grip (112) of handle assembly (100) is a preferred location to locate handle transceiver (604) as distally from handle controller (602) and motor (160) as possible so as to reduce the potential for interference. In some examples, shroud (612) can be placed between handle transceiver (604) and the other components of handle assembly (100) to further reduce radiofrequency interference from the electrical components therein. Popular radiofrequency shielding materials for shroud (612) can include aluminum, copper, plated steel, nickel silver, and the like. Since the example embodiment in FIG. 10 has a handle transceiver (604) positioned distal to handle controller (602), the embodiment can include connector (606) to electrically connect handle transceiver (604) and handle controller (602).

Figure 11:
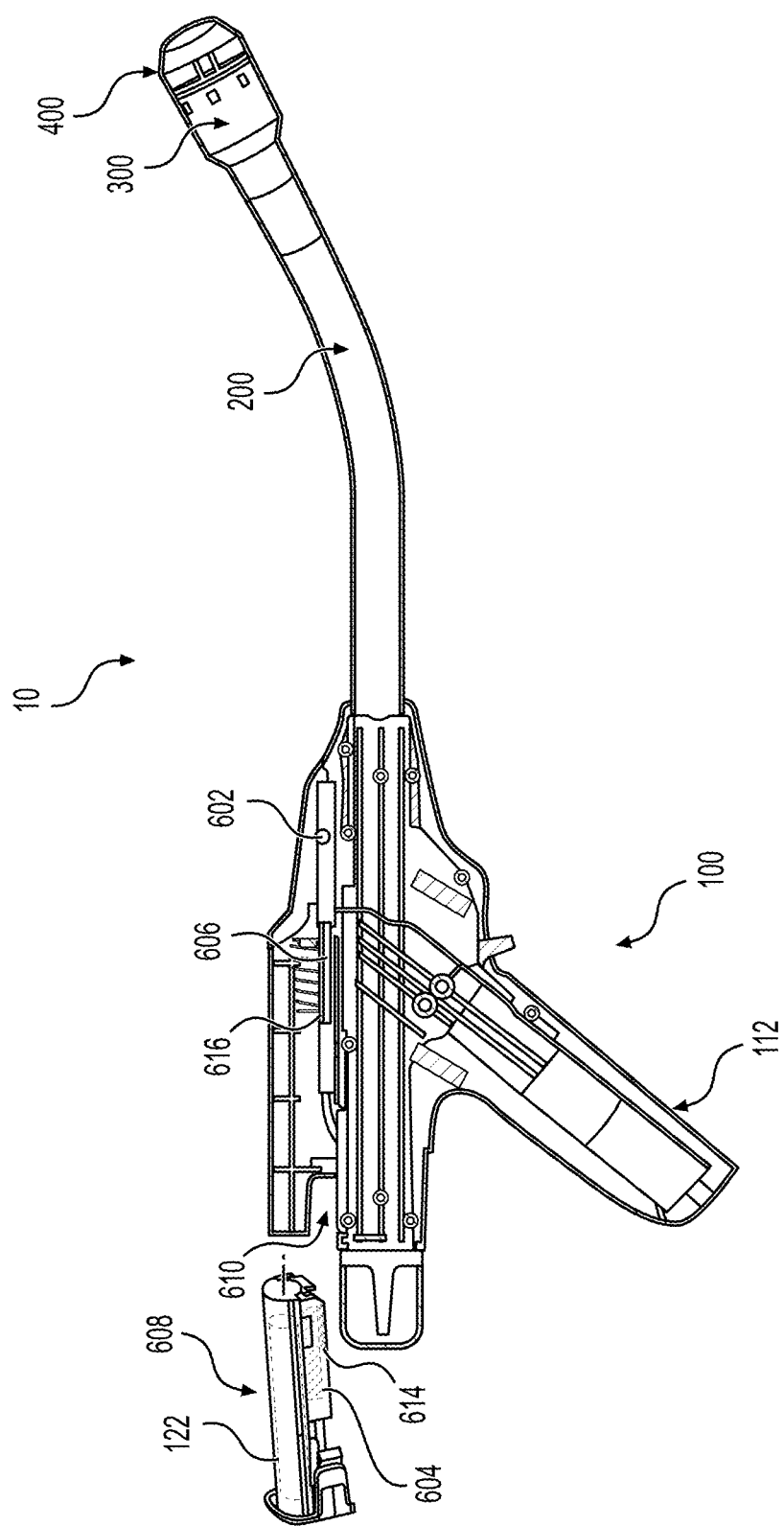
FIG. 11 depicts a circular stapler with a handle transceiver positioned within a battery housing, according to one aspect of the present disclosure.

FIG. 11 depicts circular stapler (10) with handle transceiver (604) positioned within battery housing (608), according to one aspect of the present disclosure. As described above, battery housing (608) of battery pack (120) may be removably coupled with handle assembly (100) through a snap fit or in any other suitable fashion. Battery housing (608) and handle assembly (100) may have complementary electrical contacts, pins and sockets, and/or other features that provide paths for electrical communication between battery pack (120) and handle assembly (100). For example, circular stapler (10) can include first connector (614) positioned on the battery housing (608) and which is in electrical communication with handle transceiver (604) that is positioned on or within battery housing (608). Handle assembly (100) can include a second connector (616) positioned within housing cavity (610) and which is in electrical communication with handle controller (602). First connector (614) and second connector (616) are configured to contact one another when battery housing (608) is positioned the housing cavity (610). This connection enables handle controller (602) to send and receive signals to and from handle transceiver (604). Second connector (616) can be electrically connected to handle controller (602) via connector (606) (as shown), or alternatively second connector (616) can be positioned on the same circuit board that comprises handle controller (602). The location of handle transceiver (604) in FIG. 10 also allows for the transceiver to be positioned on the upper part of handle assembly (100) such that the transceiver has a clear and direct path to anvil (400) positioned within the patient. As discussed above, shaft assembly (200) can include preformed curved section (212) that is configured to facilitate positioning of stapling head assembly (300) within the patient's colon, and the curve can help to further align anvil (400) in a direct path, less obstructed to handle transceiver (604).

Figure 12:
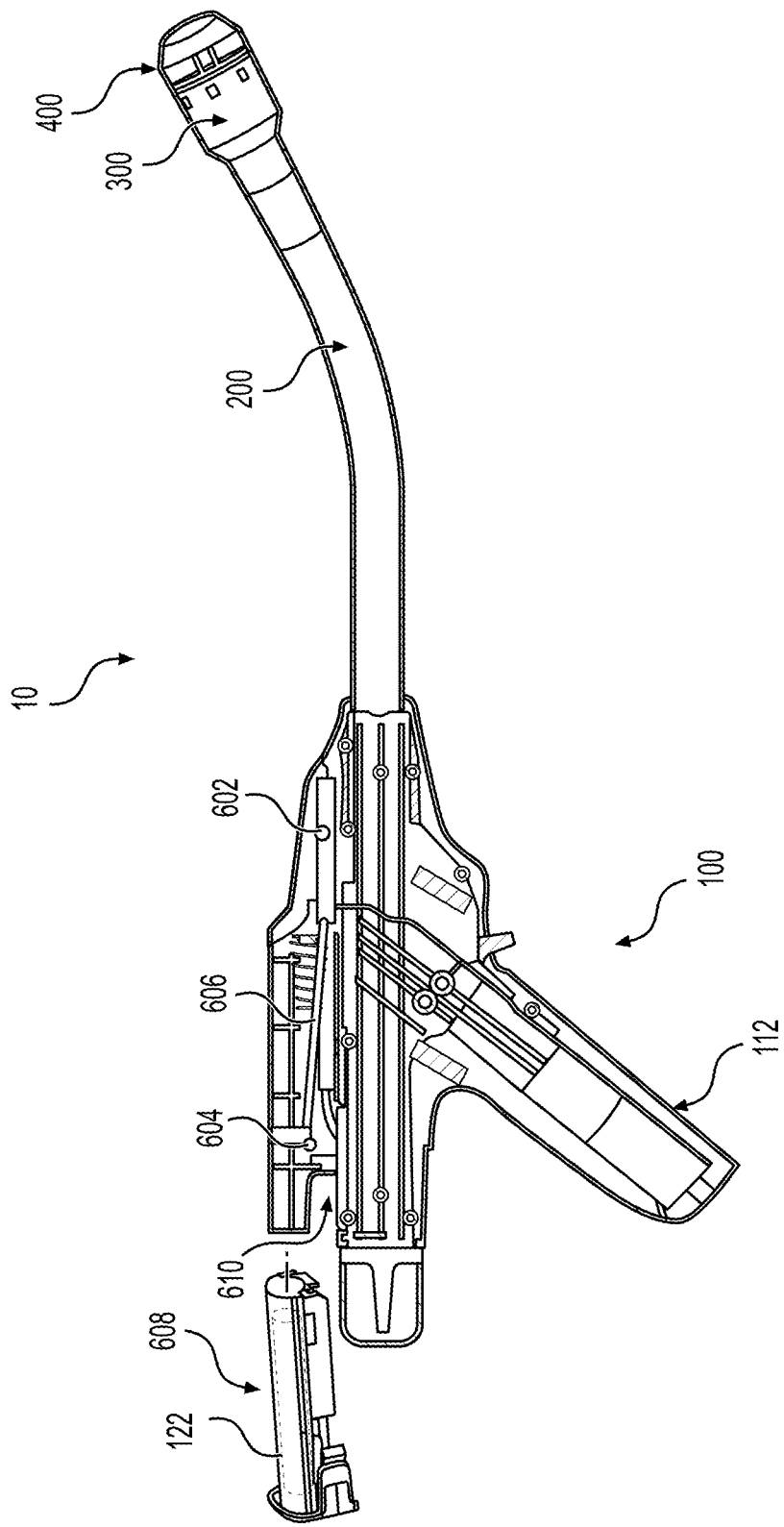
FIG. 12 depicts a circular stapler with a handle transceiver positioned within a housing cavity, according to one aspect of the present disclosure.
Figure 13:
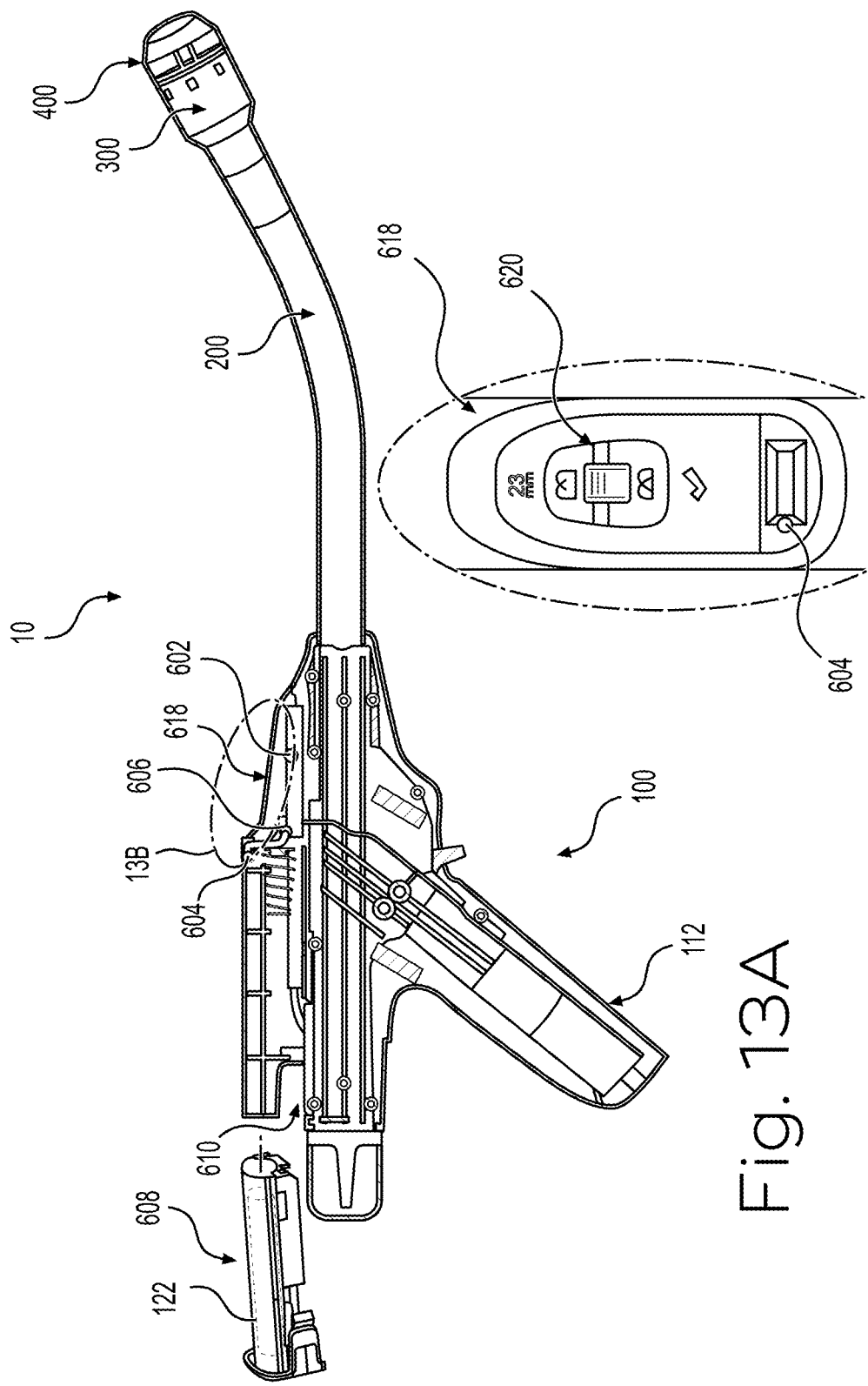
FIG. 13A depicts a circular stapler with a handle transceiver positioned on a display panel, according to one aspect of the present disclosure.
FIG. 13B provides a detail view of the display panel, according to one aspect of the present disclosure.

FIG. 12 depicts circular stapler (10) with handle transceiver (604) positioned within housing cavity (610), according to one aspect of the present disclosure. The example shown in FIG. 12 is similar to that which was shown and described with respect to FIG. 11. The difference here is that handle transceiver (604) can be securely positioned within housing cavity (610) such that it is not removable with battery housing (608). In this configuration, therefore, need not include first connector (614) and second connector (616), but instead handle transceiver (604) can be electrically connected to handle controller (602) via connector (606) (as shown).

FIG. 13A depicts circular stapler (10) with handle transceiver (604) positioned on display panel (618), and FIG. 13B provides a detail view of display panel (618), according to one aspect of the present disclosure. Display panel (618) can be positioned superficially on the housing of handle assembly (100), at the top of handle assembly (100), and proximate housing cavity (610), as shown. Display panel (618) can include display (620) that provides information about circular stapler (10) (e.g., information about the status of firing, information about status of staples (90), etc.). Display (620) can be a light-emitting diode (LED), liquid crystal display (LCD), and the like. Handle transceiver (604) can be positioned proximate display panel (618). A handle transceiver (604) positioned as such can therefore be positioned proximate handle controller (602) so as to provide a short connection to the controller, and in some instances handle transceiver (604) and at least a portion of display (620) can be positioned on the same circuit board that comprises handle controller (602). Further, the location of handle transceiver (604) in FIGS. 13A and 13B allows for the transceiver to be positioned on the upper part of handle assembly (100) such that the transceiver has a clear and direct path to anvil (400) positioned within the patient. As discussed above, shaft assembly (200) can include preformed curved section (212) that is configured to facilitate positioning of stapling head assembly (300) within the patient's colon, and the curve can help to further align anvil (400) in a direct path, less obstructed to handle transceiver (604).

Figure 14:
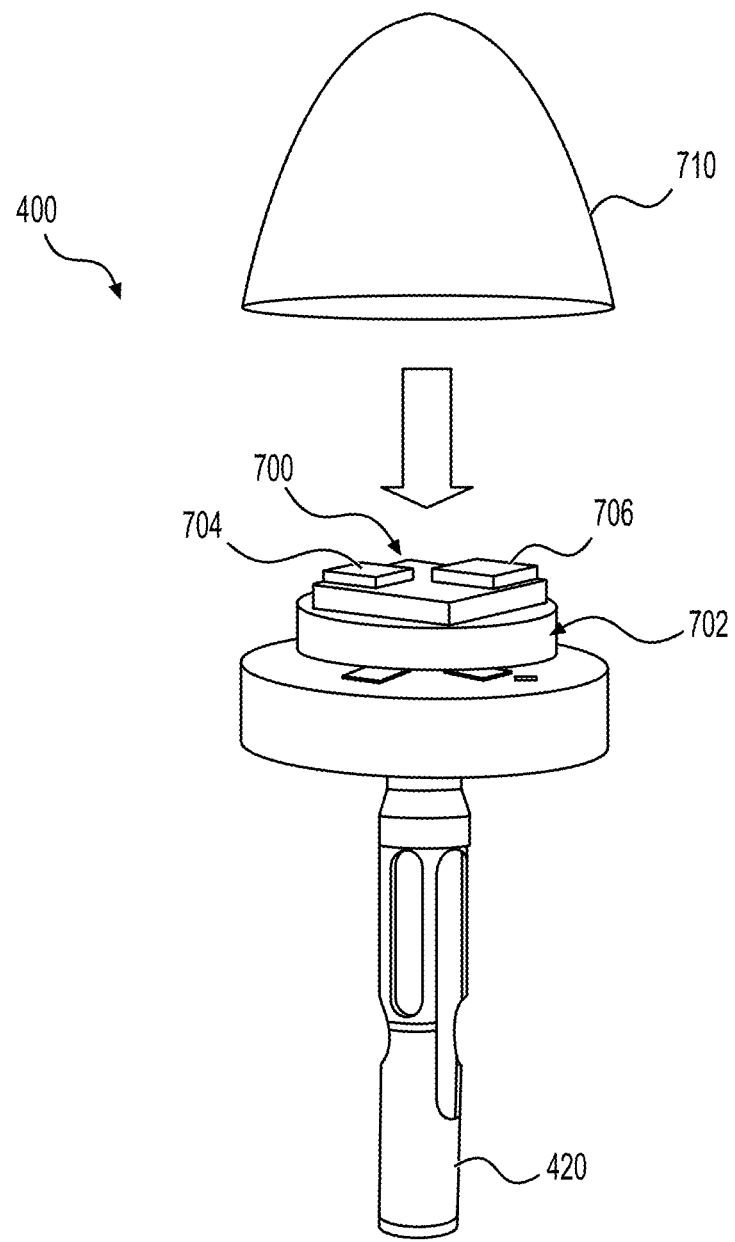
FIG. 14 depicts an anvil with an anvil circuit board, according to one aspect of the present disclosure.

FIG. 14 depicts anvil (400) with anvil circuit board (700), according to one aspect of the present disclosure. Anvil (400) can include components that made anvil (400) a "smart" component of circular stapler (10). As such, anvil (400) can be an integrated component that can operate separately from handle assembly (100), which is required since anvil (400) is detachably attachable with respect to head assembly (300). Anvil (400) therefore includes power source (702), processor (704), memory (708) (see FIG. 16), and anvil transceiver (706), each of which is positioned on anvil circuit board (700); the electrical components can be sealed within anvil (400) with anvil cap (710). Power source (702) can be a battery, such as a disposable or rechargeable lithium battery and the like. Anvil (400) can also include one or more sensors to detect status at the anvil (400). For example, anvil (400) can include one or more position sensors (712), which can include one or more of a gyroscopic sensor, an accelerometer, or a proximity sensor operable to detect an orientation of anvil (400) within the patient. A gyroscopic sensor and/or an accelerometer can be used to determine how the anvil (400) is oriented inside the patient. Since it is one aspect to insert trocar (330) into lumen (422), it can be helpful to be able to visualize the three dimensional orientation (similar to roll, pitch, and yaw) of the anvil (400) inside the patient so that trocar (330) and anvil (400) can be positioned to be aligned. A position sensor (712) that includes a gyroscopic sensor and/or an accelerometer can help to achieve this visualization goal. In some examples, handle assembly (100) can also include a position sensor such as a gyroscopic sensor and/or an accelerometer. In this example, the position sensors in handle assembly (100) can generate information about its orientation, the position sensors (712) in anvil (400) can generate information about its orientation, and both sets of information can be relayed to external hub (902) to assist in aligning trocar (330) and lumen (422).

A proximity sensor acting as a position sensor (712) can be used to determine how close anvil (400) may be to head assembly (300) during operation, since it is one objective to couple anvil (400) to head assembly (300) as described above-which is not contemplated in the case of a linear stapler, for example, since the end effector (anvil and staple cartridge) in a linear stapler is connected to its handle. The aforementioned proximity sensor can include, for example, an ultrasonic proximity sensor, magnetic proximity sensors, and similar proximity sensors that are able to provide proximity information even when tissue may be between anvil (400) and head assembly (300). Any position sensor (712) described herein can create sensor data comprising information related to the orientation of anvil (400). This information can be generated by position sensor (712), transmitted to processor (704) to be processed, and then transmitted to anvil transceiver (706) to in turn be relayed to handle transceiver (604). Handle transceiver (604) can then send the generated sensor data to external hub (902) so that it can be displayed to the user. Anvil (400) can include other types of sensors, as will be described below with respect to FIG. 15.

Figure 15:
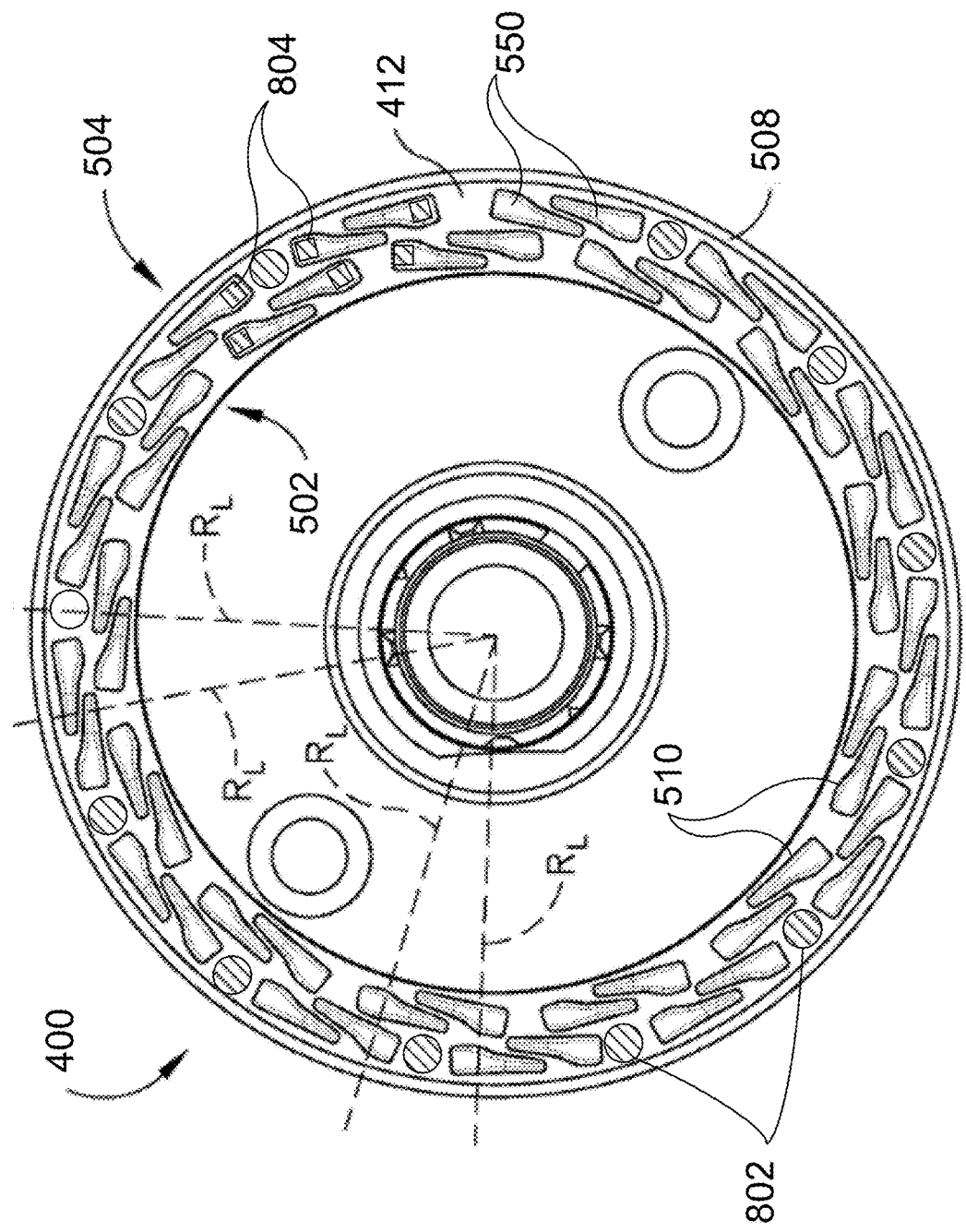
FIG. 15 depicts a bottom plan view of an exemplary anvil that may be used with the circular stapler of FIG. 1, according to one aspect of the present disclosure.

FIG. 15 shows an exemplary anvil (400) that may be used with a version of circular stapler (10). Anvil (400) of the present example comprises anvil surface (412) that defines an inner annular array (502) of staple forming pockets (510) and an outer annular array (504) of staple forming pockets (550) (both similar to aforementioned staple forming pockets (414)). Briefly, staple forming pockets (510, 550) can be arranged such that a radius line ($R_L$) extending outwardly from the center of anvil (400) passes through the region of entry surface of staple forming pocket (510) and through the region of entry surface of staple forming pocket (550). Thus, staple forming pockets (510, 550) can overlap along a radial dimension. A chamfered edge (508) extends about the outer perimeter of proximal surface (506). It should be understood that anvil (400) may be secured to trocar (330), that proximal surface (506) may be used to compress tissue against deck surface (322), and that staple driver (352) may drive staples (90) through tissue into staple forming pockets (510,550) in order to thereby form staples (90) in the tissue.

Anvil (400) can include surface sensor (802) positioned on the anvil surface (412). Surface sensor (802) is operable to detect contact of tissue upon the anvil surface (412), generate a signal with information related to the contact, transmit the generated signal to processor (704) to be processed, such that the signal can be transmitted to anvil transceiver (706) to in turn be relayed to handle transceiver (604). This information can be used to determine that tissue is properly compressed between anvil surface (412) and distally presented deck surface (322) of stapling head assembly (300) (see FIG. 4). In some examples, surface sensor (802) is one of a plurality of surface sensors, and the plurality of surface sensors is configured to detect compression of tissue between anvil surface (412) and the deck surface (322). For example, surface sensor (802) can measure tissue impedances at different zones on the anvil surface (412), compare the measured tissue impedances to predetermined tissue impedance signature of the surface sensor (802), and detect an irregularity in at least one of position or orientation of the tissue between the anvil surface (412) and distally presented deck surface (322) of stapling head assembly (300) (see FIG. 4). The compression through tissue may be determined from an impedance of tissue. At various levels of compression, the impedance Z of tissue may increase or decrease. By applying a voltage V and a current I to the tissue, the impedance Z of the tissue may be determined at various levels of compression.

Anvil (400) can include a plurality of staple pocket sensors (804), each staple pocket sensor (804) positioned within one of the staple forming pockets (414,510,550). Staple pocket sensors (804) can be configured to detect contact by a staple (90), generate a signal comprising information from one or more of the plurality of staple pocket sensors (804), and transmit the generated signal to processor (704) to be processed, such that the signal can be transmitted to anvil transceiver (706) to in turn be relayed to handle transceiver (604).

Figure 16:
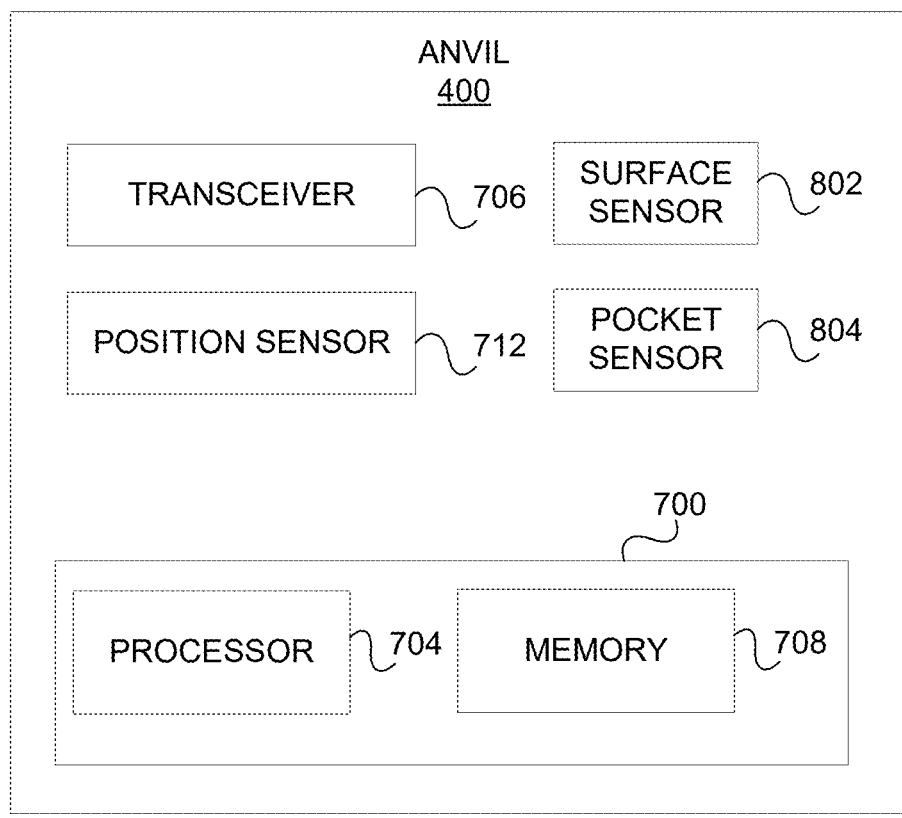
FIG. 16 is a component diagram of an example smart anvil, according to one aspect of the present disclosure.

FIG. 16 is a component diagram of an example smart anvil (400), according to one aspect of the present disclosure. As shown, anvil (400) can include processor (704), memory (708), and anvil transceiver (706). Anvil transceiver (706)—and handle transceiver (604)—can be compatible with one or more of: radio-frequency identification (RFID), near-field communication (NFC), Bluetooth™, low-energy Bluetooth™ (BLE), WiFi, or similar technologies. In some examples, the different components can have different frequencies for different purposes. For example, in one example, anvil transceiver (706) can transmit a signal at a first frequency, and handle transceiver (604) can transmit a signal at a second, different frequency. Anvil transceiver (706) can generate and transmit a lower signal frequency to handle transceiver (604) so that the signal can pass through the patient's tissue more easily; handle transceiver (604) can generate and transmit a higher signal frequency since (i) it is not trying to pass through patient tissue and (ii) it can have a frequency that is dedicated to its communication with the external hub (902) and that is different than the anvil frequency to reduce interference.

Processor (704) can include one or more of a microprocessor, microcontroller, digital signal processor, co-processor or the like or combinations thereof capable of executing stored instructions and operating upon stored data. Memory (708) can include, in some implementations, one or more suitable types of memory (e.g., such as volatile or non-volatile memory, random access memory (RAM), read only memory (ROM), programmable read-only memory (PROM), erasable programmable read-only memory (EPROM), electrically erasable programmable read-only memory (EEPROM), flash memory, and the like), for storing files including an operating system, application programs, executable instructions and data. In one embodiment, the processing techniques described herein can be implemented as a combination of executable instructions and data stored within memory (708). Memory (708) can include instructions that, when executed by processor (704), perform one or more processes consistent with the functionalities disclosed herein. Methods, systems, and articles of manufacture consistent with disclosed embodiments are not limited to separate programs or computers configured to perform dedicated tasks. For example, anvil (400) can include memory (708) that can include one or more programs to perform one or more functions of the disclosed embodiments.

Figure 17:
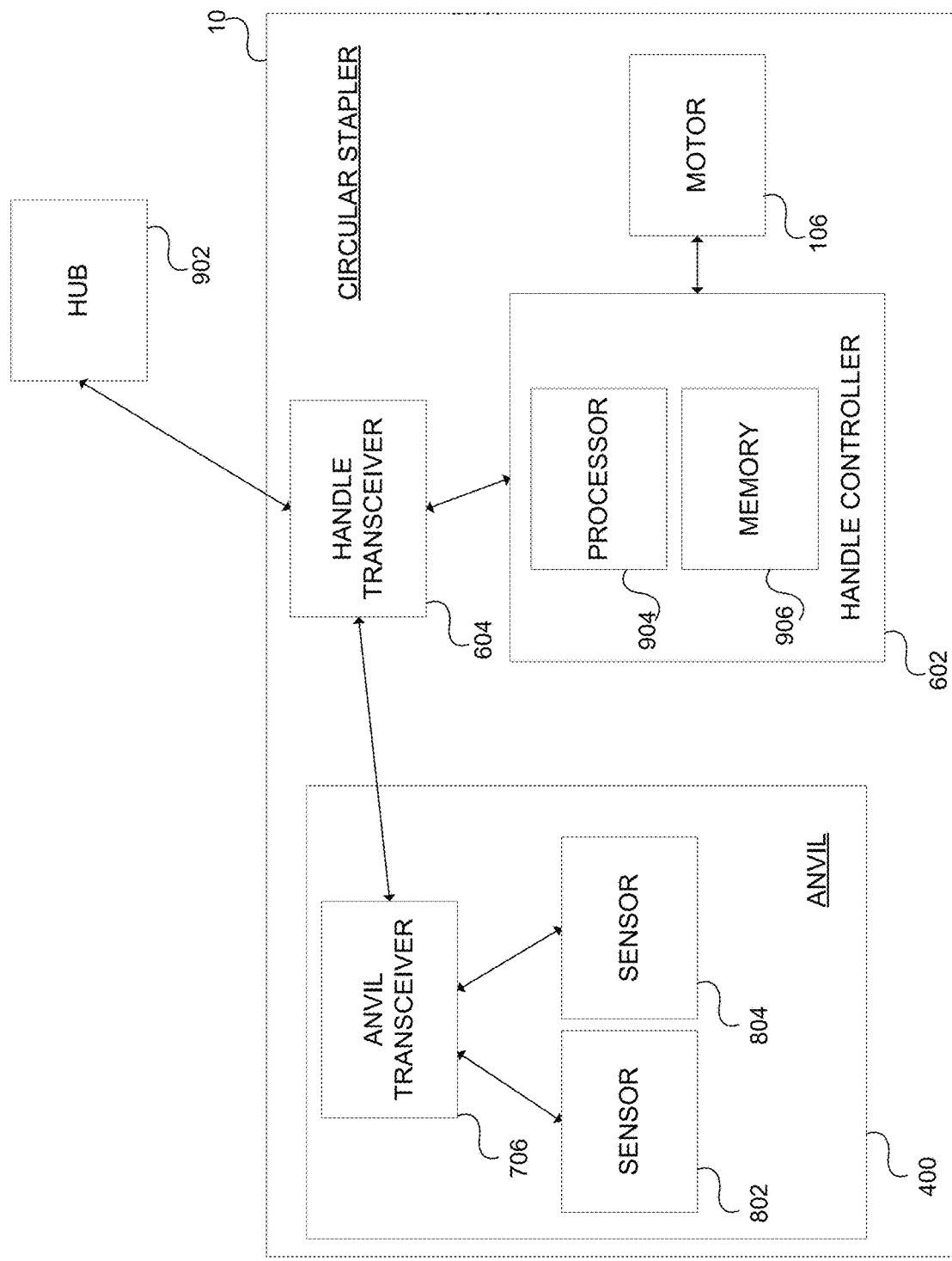
FIG. 17 depicts a system environment for an example circular stapler and external hub, according to one aspect of the present disclosure.
Figure 18:
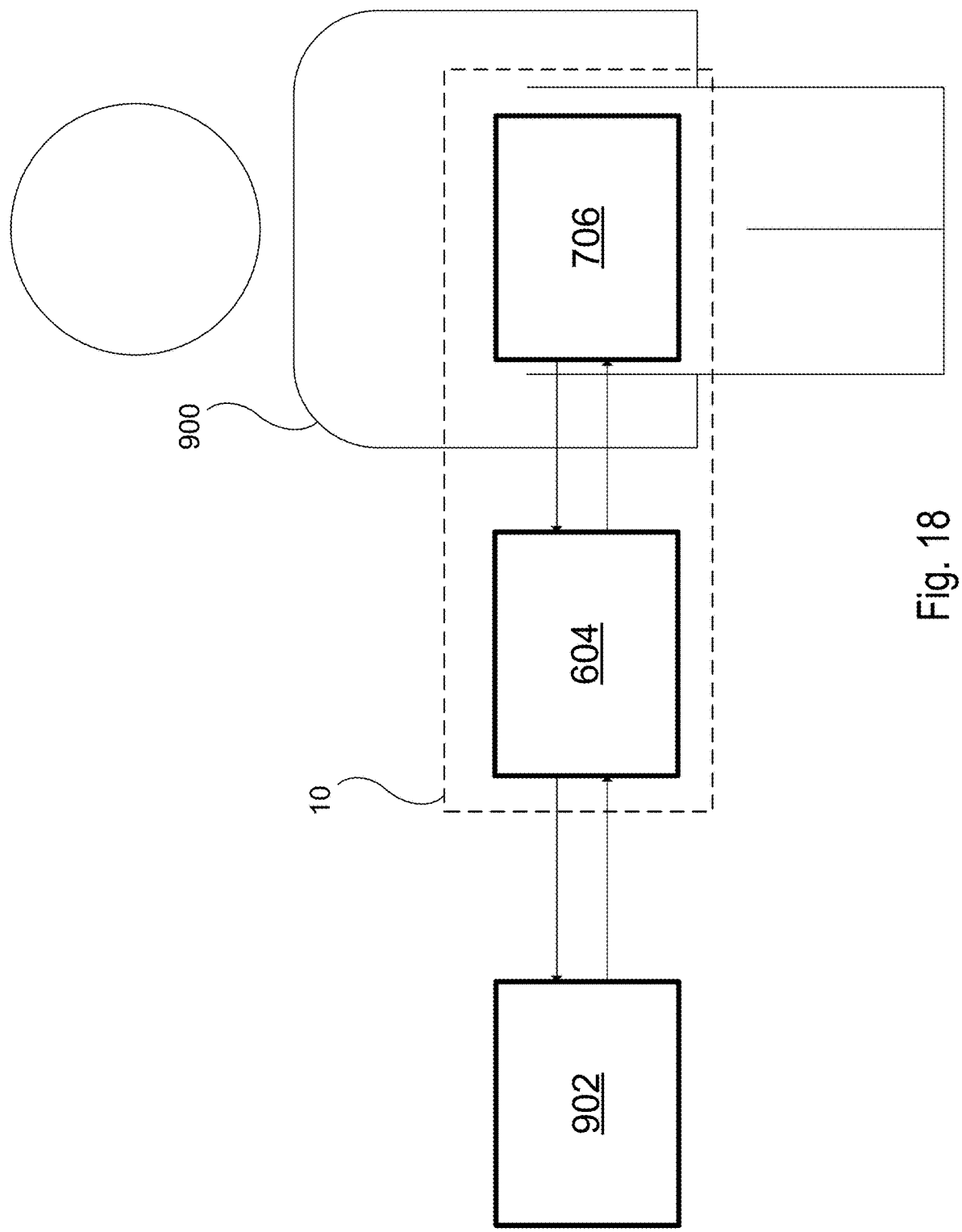
FIG. 18 is an example schematic of a smart circular stapler in use.

FIG. 17 depicts a system environment for an example circular stapler (10) and external hub (902), according to one aspect of the present disclosure. Handle controller (602) can include processor (904), which can be substantially similar to processor (704). Handle controller (602) can include memory (906), which can be substantially similar to memory (708). As described above, external hub (902) can include an external computing system with a display for providing the information received from within obstruction (900). That external hub (902) can be positioned many feet away from the location of circular stapler (10), and since the patient's tissue can obstruct signals in the normal range of operation of such devices (e.g., around 2.4 GHz for Bluetooth™ or Wi-Fi™), the obstruction may be such that the signals cannot reach hub (902). FIG. 18 is an example schematic of a smart circular stapler (10) in use. It further identifies how anvil transceiver (706) is positioned within obstruction (900) (i.e., the patient's abdomen), handle transceiver (604) is positioned outside of the obstruction (900), and external hub (902) is positioned distal to handle transceiver (604) and circular stapler (10). As described above, external hub (902) can include an external computing system with a display for providing the information received from within obstruction (900). In some examples, external hub (902) can be a component of a robotic system, and circular stapler (10) can be an attachment to the robotic system.

The technology described herein can further be implemented by any of the following numbered clauses:

Clause 1: An apparatus comprising: (A) a stapling head assembly (300); (B) an anvil (400) detachably attachable to the stapling head assembly (300); and (C) a handle assembly (100) comprising: a handle controller (602); a connector (606); and a handle transceiver (604) configured to wirelessly transmit a first signal to an external hub (902), wherein the handle transceiver (604) is separated from the handle controller (602) and is in electrical communication with the handle controller (602) via the connector (606).

Clause 2: The apparatus of Clause 1, wherein the handle assembly (100) comprises a knob (130) rotatable to adjust a gap distance between anvil surface (412) and the handle assembly (100), wherein the handle transceiver (604) is positioned within the knob (130).

Clause 3: The apparatus of Clause 1, wherein the handle assembly (100) comprises a pistol grip (112), and wherein the handle transceiver (604) is positioned within the pistol grip (112).

Clause 4: The apparatus of Clause 3, wherein the handle transceiver (604) is encased within a shroud (612) to shield the handle transceiver (604) from signal noise from a motor (160).

5: The apparatus of Clause 1, wherein the handle assembly (100) comprises: a battery housing (608) including a battery (122); and a housing cavity (610) sized to accept the battery housing (608), wherein the battery housing (608) is insertable and removable from the housing cavity (610), and wherein the handle transceiver (604) is positioned on the battery housing (608).

Clause 6: The apparatus of Clause 5, wherein the handle assembly (100) comprises: a first connector (614) positioned on the battery housing (608) and in electrical communication with the handle transceiver (604); and a second connector (616) positioned within the housing cavity (610) and in electrical communication with the handle controller (602), wherein the first connector (614) and the second (616) are configured to contact one another when the battery housing (608) is positioned within the housing cavity (610).

Clause 7: The apparatus of Clause 1, wherein the handle assembly (100) comprises: a battery housing (608) including a battery (122); and a housing cavity (610) sized to accept the battery housing (608), wherein the battery housing (608) is insertable and removable from the housing cavity (610), and wherein the handle transceiver (604) is positioned within the housing cavity (610).

Clause 8: The apparatus of Clause 1, wherein the handle assembly (100) comprises a display (620) positioned on a display panel (620) visible from an exterior of the handle assembly (100), wherein the handle transceiver (604) is positioned on the display panel (620).

Clause 9: The apparatus of Clause 1, wherein the anvil (400) is removably attached to the stapling head assembly (300) and comprises one or more sensors (802, 804, 712) configured to output signals to the handle controller (602).

Clause 10: The apparatus of Clause 9, wherein: the anvil (400) comprises an anvil transceiver (706); the one or more sensors (802, 804, 712) are configured to generate a second signal comprising first sensor data; the one or more sensors (802, 804, 712) are configured to transmit the first signal to the anvil transceiver (706); and the handle transceiver (604) is configured to communicate wirelessly with the anvil transceiver (706) and is operable as a wireless relay between the anvil transceiver (706) and the external hub (902).

Clause 11: An apparatus comprising: (A) a stapling head assembly (300) comprising: a deck surface (322); an array of staple openings (324) formed through the deck surface (322); a plurality of staples (90) associated with the array of staple openings (324), wherein the stapling head assembly (300) is operable to drive the staples (90) through the array of staple openings (324); (B) an anvil (400) detachably attachable to the stapling head assembly (300) and comprising: an anvil surface (412) configured to compress tissue against the deck surface (322), wherein the anvil surface (412) defines an array of staple forming pockets (414, 510, 550); an anvil power source (702); and an anvil transceiver (706); and (C) a handle assembly (100) comprising: a handle controller (602); and a handle transceiver (604) configured to communicate wirelessly with both the anvil transceiver (706) and an external hub (902), and wherein the handle transceiver (604) is operable as a wireless relay to receive a first signal from the anvil transceiver (706) and transmit a second signal to the external hub (902).

Clause 12: The apparatus of Clause 11, wherein the anvil (400) further comprises a position sensor (712) operable to detect an orientation of the anvil (400) within a patient, and wherein the first signal comprises information related to the orientation of the anvil (400).

Clause 13: The apparatus of Clause 11, wherein the anvil (400) further comprises a surface sensor (802) positioned on the anvil surface (412), wherein the surface sensor (802) is operable to detect contact of tissue upon the anvil surface (412), and wherein the first signal comprises information related to the contact.

Clause 14: The apparatus of Clause 13, wherein the surface sensor (802) is one of a plurality of surface sensors, and wherein the plurality of surface sensors is configured to detect compression of tissue between the anvil surface (412) and the deck surface (322).

Clause 15: The apparatus of Clause 11, wherein the anvil (400) further comprises a plurality of staple pocket sensors (804), each staple pocket sensor (804) positioned within one of the staple forming pockets (414, 510, 550) and configured to detect contact by a staple (90), and wherein the first signal comprises information from one or more of the plurality of staple pocket sensors (804).

Clause 16: The apparatus of Clause 11, wherein the handle assembly (100) comprises a knob (130) rotatable to adjust a gap distance between anvil surface (412) and the deck surface (322), wherein the handle transceiver (604) is positioned within the knob (130).

Clause 17: The apparatus of Clause 11, wherein the handle assembly (100) comprises a pistol grip (112), and wherein the handle transceiver (604) is positioned within the pistol grip (112).

Clause 18: The apparatus of Clause 17, wherein the handle transceiver (604) is encased within a shroud (612) to shield the handle transceiver (604) from signal noise from a motor (160).

Clause 19: The apparatus of Clause 11, wherein the handle assembly (100) comprises: a battery housing (608) including a battery (122); and a housing cavity (610) sized to accept the battery housing (608), wherein the battery housing (608) is insertable and removable from the housing cavity (610), and wherein the handle transceiver (604) is positioned on the battery housing (608).

Clause 20: The apparatus of Clause 19, wherein the handle assembly (100) comprises: a first connector (614) positioned on the battery housing (608) an in electrical communication with the handle transceiver (604); and a second connector (616) positioned within the housing cavity (610) and in electrical communication with the handle controller (602), wherein the first connector (614) and the second connector (616) are configured to contact one another when the battery housing (608) is positioned within the housing cavity (610).

Clause 21: The apparatus of Clause 11, wherein the handle assembly (100) comprises: a battery housing (608) including a battery (122); and a housing cavity (610) sized to accept the battery housing (608), wherein the battery housing (608) is insertable and removable from the housing cavity (610), and wherein the handle transceiver (604) is positioned within the housing cavity (610).

Clause 22: The apparatus of Clause 11, wherein the handle assembly (100) comprises a display (620) positioned on a display panel (620) visible from an exterior of the handle assembly (100), wherein the handle transceiver (604) is positioned on the display panel (620).

Clause 23: The apparatus of Clause 11, wherein the first signal and the second signal are transmitted at different frequencies.

Clause 24: An apparatus comprising: (A) a stapling head assembly (300); (B) an anvil (400) detachably attachable to the stapling head assembly (300) and comprising an anvil transceiver (706) and one or more sensors (802, 804, 712), the one or more sensors (802, 804, 712) configured to generate a first signal comprising first sensor data, and transmit the first signal to the anvil transceiver (706) for transmission by the anvil transceiver (706); and (C) a handle assembly (100) comprising: a handle controller (602); and a handle transceiver (604) configured to communicate wirelessly with the anvil transceiver (706) and receive the first signal.

Clause 25: The apparatus of Clause 24, wherein the handle transceiver (604) is operable as a wireless relay to receive the first signal from the anvil transceiver (706) and transmit a second signal to an external hub (902).

Clause 26: The apparatus of Clause 25, wherein the second signal comprises the first sensor data.

Clause 27: The apparatus of Clause 25, wherein the first signal and the second signal are transmitted at different frequencies.

Clause 28: The apparatus of Clause 24, wherein one or more sensors (802, 804, 712) comprises a position sensor (712) operable to detect an orientation of the anvil (400) within a patient, and wherein first sensor data comprises information related to the orientation of the anvil (400).

Clause 29: The apparatus of Clause 24, wherein the handle assembly (100) comprises: a battery housing (608) including a battery (122); and a housing cavity (610) sized to accept the battery housing (608), wherein the battery housing (608) is insertable and removable from the housing cavity (610), and wherein the handle transceiver (604) is positioned on the battery housing (608).

Clause 30: The apparatus of Clause 24, wherein the handle assembly (100) comprises a display (620) positioned on a display panel (620) visible from an exterior of the handle assembly (100), wherein the handle transceiver (604) is positioned on the display panel (620).

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometric s, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

The invention is not necessarily limited to the examples described, which can be varied in construction and detail. The terms "distal" and "proximal" are used throughout the preceding description and are meant to refer to a positions and directions relative to the physician or user holding circular stapler 10. As such, "distal" or distally" refer to a position distant to or a direction away from the person gripping circular stapler 10. Similarly, "proximal" or "proximally" refer to a position near or a direction towards the person grasping pistol grip 112 (i.e., toward an operator of circular stapler 10). Furthermore, the singular forms "a," "an," and "the" include plural referents unless the context clearly dictates otherwise. Furthermore, the use of "couple", "coupled", or similar phrases should not be construed as being limited to a certain number of components or a particular order of components unless the context clearly dictates otherwise.

As used herein, the terms "about" or "approximately" for any numerical values or ranges indicate a suitable dimensional tolerance that allows the part or collection of components to function for its intended purpose as described herein. More specifically, "about" or "approximately" may refer to the range of values ±10% of the recited value, e.g., "about 90%" may refer to the range of values from 80.001% to 99.999%.

In describing example embodiments, terminology has been resorted to for the sake of clarity. As a result, not all possible combinations have been listed, and such variants are often apparent to those of skill in the art and are intended to be within the scope of the claims which follow. It is intended that each term contemplates its broadest meaning as understood by those skilled in the art and includes all technical equivalents that operate in a similar manner to accomplish a similar purpose without departing from the scope and spirit of the invention. It is also to be understood that the mention of one or more steps of a method does not preclude the presence of additional method steps or intervening method steps between those steps expressly identified. Similarly, some steps of a method can be performed in a different order than those described herein without departing from the scope of the disclosed technology.

The invention claimed is:

1. An apparatus comprising:
   (A) a stapling head assembly;
   (B) an anvil detachably attachable to the stapling head assembly; and
   (C) a handle assembly comprising:
      a handle controller;
      a connector; and
      a handle transceiver configured to wirelessly transmit a first signal to an external hub, wherein the handle transceiver is separated from the handle controller and is in electrical communication with the handle controller via the connector.

2. The apparatus of claim 1, wherein the handle assembly comprises a knob rotatable to adjust a gap distance between anvil surface and the handle assembly, wherein the handle transceiver is positioned within the knob.

3. The apparatus of claim 1, wherein the handle assembly comprises a pistol grip, and wherein the handle transceiver is positioned within the pistol grip.

4. The apparatus of claim 3, wherein the handle transceiver is encased within a shroud to shield the handle transceiver from signal noise from a motor.

5. The apparatus of claim 1, wherein the handle assembly comprises:
   a battery housing including a battery; and
   a housing cavity sized to accept the battery housing,
   wherein the battery housing is insertable and removable from the housing cavity, and
   wherein the handle transceiver is positioned on the battery housing.

6. The apparatus of claim 5, wherein the handle assembly comprises:
   a first connector positioned on the battery housing and in electrical communication with the handle transceiver; and
   a second connector positioned within the housing cavity and in electrical communication with the handle controller,
   wherein the first connector and the second are configured to contact one another when the battery housing is positioned within the housing cavity.

7. The apparatus of claim 1, wherein the handle assembly comprises:
   a battery housing including a battery; and
   a housing cavity sized to accept the battery housing,
   wherein the battery housing is insertable and removable from the housing cavity, and
   wherein the handle transceiver is positioned within the housing cavity.

8. The apparatus of claim 1, wherein the handle assembly comprises a display positioned on a display panel visible from an exterior of the handle assembly, wherein the handle transceiver is positioned on the display panel.

9. The apparatus of claim 1, wherein the anvil is removably attached to the stapling head assembly and comprises one or more sensors configured to output signals to the handle controller.

10. The apparatus of claim 9, wherein:
    the anvil comprises an anvil transceiver;
    the one or more sensors are configured to generate a second signal comprising first sensor data;
    the one or more sensors are configured to transmit the first signal to the anvil transceiver; and
    the handle transceiver is configured to communicate wirelessly with the anvil transceiver and is operable as a wireless relay between the anvil transceiver and the external hub.

11. An apparatus comprising:
    (A) a stapling head assembly comprising:
       a deck surface;
       an array of staple openings formed through the deck surface;
       a plurality of staples associated with the array of staple openings, wherein the stapling head assembly is operable to drive the staples through the array of staple openings;
    (B) an anvil detachably attachable to the stapling head assembly and comprising:
       an anvil surface configured to compress tissue against the deck surface, wherein the anvil surface defines an array of staple forming pockets;
       an anvil power source; and
       an anvil transceiver; and
    (C) a handle assembly comprising:
       a handle controller; and
       a handle transceiver configured to communicate wirelessly with both the anvil transceiver and an external hub, and wherein the handle transceiver is operable as a wireless relay to receive a first signal from the anvil transceiver and transmit a second signal to the external hub.

12. The apparatus of claim 11, wherein the anvil further comprises a position sensor operable to detect an orientation of the anvil within a patient, and wherein the first signal comprises information related to the orientation of the anvil.

13. The apparatus of claim 11, wherein the anvil further comprises a surface sensor positioned on the anvil surface, wherein the surface sensor is operable to detect contact of tissue upon the anvil surface, and wherein the first signal comprises information related to the contact.

14. The apparatus of claim 13, wherein the surface sensor is one of a plurality of surface sensors, and wherein the plurality of surface sensors is configured to detect compression of tissue between the anvil surface and the deck surface.

15. The apparatus of claim 11, wherein the anvil further comprises a plurality of staple pocket sensors, each staple pocket sensor positioned within one of the staple forming pockets and configured to detect contact by a staple, and wherein the first signal comprises information from one or more of the plurality of staple pocket sensors.

16. The apparatus of claim 11, wherein the handle assembly comprises a knob rotatable to adjust a gap distance between anvil surface and the deck surface, wherein the handle transceiver is positioned within the knob.

17. The apparatus of claim 11, wherein the handle assembly comprises a pistol grip, and wherein the handle transceiver is positioned within the pistol grip.

18. The apparatus of claim 17, wherein the handle transceiver is encased within a shroud to shield the handle transceiver from signal noise from a motor.

19. The apparatus of claim 11, wherein the handle assembly comprises:
   a battery housing including a battery; and
   a housing cavity sized to accept the battery housing,
   wherein the battery housing is insertable and removable from the housing cavity, and
   wherein the handle transceiver is positioned on the battery housing.

20. The apparatus of claim 19, wherein the handle assembly comprises:
   a first connector positioned on the battery housing an in electrical communication with the handle transceiver; and
   a second connector positioned within the housing cavity and in electrical communication with the handle controller,
   wherein the first connector and the second connector are configured to contact one another when the battery housing is positioned within the housing cavity.

* * * * *